US010519092B2

(12) United States Patent
Boehm et al.

(10) Patent No.: US 10,519,092 B2
(45) Date of Patent: *Dec. 31, 2019

(54) 3,6-DICHLOROSALICYLIC ACID COMPOUNDS AND RELATED SYNTHETIC PROCESSES

(71) Applicant: Monsanto Technology LLC, St. Louis, MO (US)

(72) Inventors: Terri L. Boehm, Ballwin, MO (US); Mangesh Bore, Midland, MI (US); Jeffery N. Carroll, St. Louis, MO (US); G. Davis Harris, Jr., Chesterfield, MO (US); Matthew D. McReynolds, St. Louis, MO (US); Justin R. Struble, Ballwin, MO (US); Daniel P. Walker, Augusta, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/820,512

(22) Filed: Nov. 22, 2017

(65) Prior Publication Data

US 2018/0155265 A1    Jun. 7, 2018

Related U.S. Application Data

(63) Continuation of application No. 15/313,728, filed as application No. PCT/US2015/033894 on Jun. 3, 2015, now Pat. No. 9,856,201.

(60) Provisional application No. 62/111,303, filed on Feb. 3, 2015, provisional application No. 62/042,068, filed on Aug. 26, 2014, provisional application No. 62/007,578, filed on Jun. 4, 2014.

(51) Int. Cl.
| | | |
|---|---|---|
| C07C 51/363 | (2006.01) | |
| C07C 51/29 | (2006.01) | |
| C07C 67/307 | (2006.01) | |
| C07C 67/317 | (2006.01) | |
| C07C 69/92 | (2006.01) | |
| C07C 69/88 | (2006.01) | |
| C07C 51/367 | (2006.01) | |
| C07C 51/377 | (2006.01) | |
| C07C 67/035 | (2006.01) | |

(52) U.S. Cl.
CPC ............ *C07C 51/363* (2013.01); *C07C 51/29* (2013.01); *C07C 51/367* (2013.01); *C07C 51/377* (2013.01); *C07C 67/035* (2013.01); *C07C 67/307* (2013.01); *C07C 67/317* (2013.01); *C07C 69/88* (2013.01); *C07C 69/92* (2013.01)

(58) Field of Classification Search
CPC ... C07C 51/363; C07C 51/367; C07C 51/377; C07C 67/035
See application file for complete search history.

(56) References Cited

U.S. PATENT DOCUMENTS

| | | | |
|---|---|---|---|
| 3,013,054 A | 12/1961 | Richter | |
| 3,062,877 A | 11/1962 | Hanna | |
| 3,345,157 A | 10/1967 | Richter | |
| 3,444,192 A | 5/1969 | Newcomer | |
| 3,728,403 A | 4/1973 | Ross | |
| 3,928,432 A | 12/1975 | Becher et al. | |
| 3,969,403 A | 7/1976 | Becher et al. | |
| 4,161,611 A | 7/1979 | Kim | |
| 4,232,172 A | 11/1980 | Becher et al. | |
| 4,308,395 A | 12/1981 | Manfre et al. | |
| 5,194,666 A * | 3/1993 | Sedlak | C07C 51/363 560/62 |
| 5,442,092 A * | 8/1995 | Chopdekar | C07C 69/88 560/65 |
| 5,719,104 A | 2/1998 | Kilama et al. | |
| 6,268,506 B1 | 7/2001 | Crispino et al. | |
| 9,856,201 B2 * | 1/2018 | Boehm | C07C 51/367 |
| 2005/0037922 A1 | 2/2005 | Bickers et al. | |
| 2007/0287711 A1 * | 12/2007 | Arnold | C07D 471/04 514/249 |
| 2009/0143352 A1 * | 6/2009 | Arnold | C07D 471/04 514/210.18 |
| 2010/0041555 A1 | 2/2010 | Tsukamoto et al. | |

(Continued)

FOREIGN PATENT DOCUMENTS

| | | |
|---|---|---|
| CN | 1830942 A | 9/2006 |
| CN | 102838483 A | 12/2012 |

(Continued)

OTHER PUBLICATIONS

Adibi, Hadi, et al., "A convenient and regioselective oxidative bromination of electron-rich aromatic rings using potassium bromide and benzyltriphenylphosphonium peroxymonosulfate under nearly neutral reaction conditions", Tetrahedron Letters 48 (2007) 1255-1259.

Ashar, N.G., "A Practical Guide to the Manufacture of Sulfuric Acid, Oleums, and Sulfonating Agents", Springer International Publishing AG (2013).

Dowd, Christopher D. and Paul D. Brenton, "Synthesis and Evaluation of Diaryl Oxalate Esters for Low-Intensity Chemiluminescent Illumination", Aust. J. Chem. (1984), 37, 73-86.

Eckstein, et al., "Comparison of the Methods of 3, 6-Dichloro-2-Methoxybenzic Acid (Dicamba)-Preparation", Przem. Chem. 1979, 58 (10), 533-536 (Pol.) (English Abstract Only).

Farinholt, Larkin H. et al., "The Halogenation of Salicylic Acid", J. Am. Chem. Soc. (1940), 62, 1237-1241.

(Continued)

*Primary Examiner* — Amy C Bonaparte
(74) *Attorney, Agent, or Firm* — Stinson LLP; Eric C. Robert

(57) ABSTRACT

The present disclosure relates, in general, to 5-halo-3,6-dichlorosalicylic acid compounds, 5-halo-3,6-dichlorosalicyaldehyde compounds, processes for preparing 5-halo-3,6-dichlorosalicylic acid compounds, processes for preparing 5-halo-3,6-dichlorosalicyaldehyde compounds, processes for preparing 3,6-dichlorosalicylic acid compounds, and processes that employ such compounds as intermediates in the preparation of the herbicide dicamba.

18 Claims, No Drawings

(56) References Cited

U.S. PATENT DOCUMENTS

2011/0224439 A1     9/2011    Menges et al.
2012/0035053 A1     2/2012    Matthews et al.

FOREIGN PATENT DOCUMENTS

| | | |
|---|---|---|
| CN | 102942474 A | 2/2013 |
| CN | 102125035 B | 7/2013 |
| WO | 2013174947 A1 | 11/2013 |

OTHER PUBLICATIONS

Hewitt, John Theodore et al., "The Bromination of Phenols.", J. Chem. Soc. Trans. 1904, 85, 1225-1230.

Hussey, Allen S. and Wilk, I.J., "The Reaction of Magnesium with 2,4-Dibromoanisole", J. Am. Chem Soc, 1950, 72, 830-832.

Larock, Richard C., "Comprehensive Organic Transformations", (Wiley-VCH Verlag GmbH 1999).

Mendonça, Gabriela Fonseca et al., "Trichloroisocyanuric acid in 98% sulfuric acid: A superelectrophilic medium for chlorination of deactivated arenes", Applied Catalysis A: General 401 (2011), 176-181.

Romanowski et al., "Use of 2, 6-Dichlorobenzonitrile (Dichlobenil) as a Raw-Material for Synthesis of Herbicides, Derivatives of Benzoic-Acid", Prezem. Chem. 54(1 ), pp. 26-31 (1975).

Chen, Xiao-Meng and Zhang, Yong, "Study on the O-Alkylation for Synthesis of 3,6-dichlorosalicylic Acid by Chloromethane", Huangong Shikan 2002, 16 (12) 45-48 (Ch.) (English Abstract Only).

Zhang, Yong et al., "The Study on the Preparation of Dicamba", Nongyao 2002, 41 (7), 15-17 (Ch.) (English Abstract Only).

Zhang, Xiaobo et al., "The Synthesis of Herbicides Dicamba", Nongyao 2002, 41 (11 ), 13-14 (Ch.) (English Abstract Only).

International Preliminary Report on Patentability dated Dec. 15, 2016 in related PCT Application PCT/US2015/033894, 24 pages.

International Search Report dated Aug. 18, 2015 in related PCT Applications PCT/US15/33894, 6 pages.

Written Opinion dated Aug. 18, 2015 in related PCT Applications PCT/US15/33894, 26 pages.

\* cited by examiner

3,6-DICHLOROSALICYLIC ACID COMPOUNDS AND RELATED SYNTHETIC PROCESSES

CROSS-REFERENCE TO RELATED APPLICATIONS

This application is a continuation of U.S. patent application Ser. No. 15/313,728, filed Nov. 23, 2016, now issued as U.S. Pat. No. 9,856,201, which is a 371 National Stage Application of International Application No. PCT/US2015/033894, filed Jun. 3, 2015, which claims priority to U.S. Provisional Application Ser. No. 62/007,578, filed Jun. 4, 2014, U.S. Provisional Application Ser. No. 62/042,068, filed Aug. 26, 2014, and U.S. Provisional Application Ser. No. 62/111,303, filed Feb. 3, 2015, the entirety of each of which is incorporated herein by reference.

FIELD OF THE INVENTION

The present disclosure relates, in general, to 5-bromo-3,6-dichlorosalicylic acid compounds, 5-bromo-3,6-dichlorosalicyaldehyde compounds, processes for preparing 5-bromo-3,6-dichlorosalicylic acid compounds, processes for preparing 5-bromo-3,6-dichlorosalicyaldehyde compounds, processes for preparing 3,6-dichlorosalicylic acid compounds, and processes that employ such compounds as intermediates in the preparation of the herbicide dicamba.

BACKGROUND OF THE INVENTION 3,6-Dichloro-2-methoxybenzoic acid (also known by its common name dicamba) is a highly effective and commercially important herbicide that is useful for controlling a wide variety of unwanted vegetation, including agricultural weeds. Convenient and economical methods of preparing dicamba, therefore, are of significant commercial importance.

A number of synthetic routes for the preparation of dicamba have been reported in the literature. One reported route proceeds through a 2,5-dichlorophenol intermediate as illustrated in Scheme 1 below:

Scheme 1

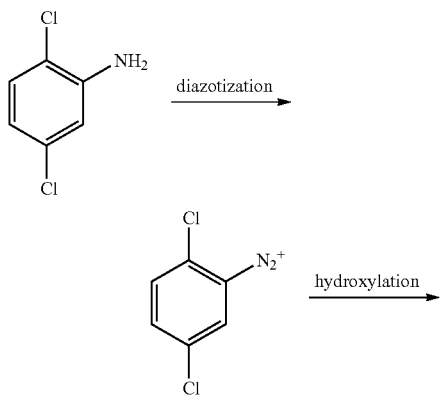

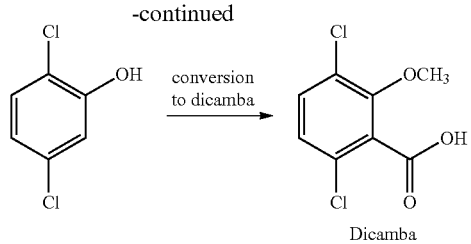

See, e.g., U.S. Pat. No. 1,161,611.

Another reported route proceeds through either a 4-bromo-3,6-dichloro-2-(hydroxymethyl) phenol intermediate or a (3-bromo-2,5-dichloro-6-methoxy-phenyl)methanol intermediate as illustrated in Scheme 2 below:

Scheme 2

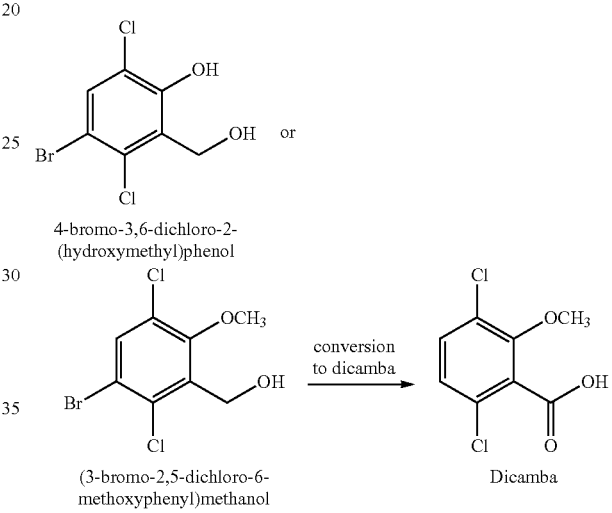

See, e.g., U.S. Pat. No. 3,928,432.

Still other reported routes employ starting materials, or proceed through intermediates, such as 2,5-dichlorophenol (see, e.g., U.S. Pat. No. 4,232,172); 2,5-dichloro-4-bromophenol (see, e.g., U.S. Pat. No. 3,728,403); 1,2,4-trichlorobenzene (see, e.g., U.S. Pat. No. 3,013,054), 2,3,6-trichlorobenzoic acid (see, e.g., U.S. Pat. No. 3,444,192); or 2,6-dichlorobenzonitrile (see, e.g., Romanowski et al., Prezem. Chem. 54(1), pp. 26-31 (1975)).

As compared to currently known processes, however, the processes of the present disclosure provide one or more advantages in the large-scale manufacture of dicamba with respect to cost and/or availability of starting materials, throughput and/or required processing steps (such as hazardous processing steps and/or separation/purification steps), equipment requirements (such as high pressure and temperature reactors), reaction conditions, reaction times, yield, energy consumption, capital costs, and the like.

BRIEF DESCRIPTION OF THE INVENTION

The present disclosure relates to 5-bromo-3,6-dichlorosalicylic acid compounds, 5-bromo-3,6-dichlorosalicyaldehyde compounds, 3,6-dichlorosalicylic acid compounds, processes for preparing such compounds, and processes for converting such compounds to dicamba.

In one aspect, the present disclosure relates to a process for the preparation of a compound corresponding in structure to Formula (III):

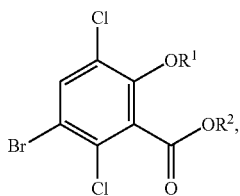

or a salt thereof, the process comprising:

contacting a compound corresponding in structure to Formula (II):

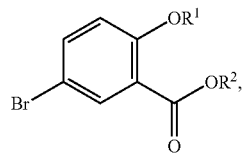

or a salt thereof, with a chlorinating agent in an acidic reaction medium to provide the compound or salt of Formula (III);

wherein $R^1$ is hydrogen or $C_{1-6}$-alkyl; and $R^2$ is hydrogen or $C_{1-6}$-alkyl.

In another embodiment, the present disclosure relates to a process for the preparation of a compound corresponding in structure to Formula (III):

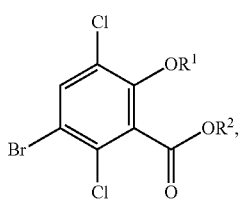

or a salt thereof, the process comprising:

contacting a compound corresponding in structure to Formula (I):

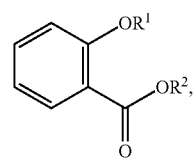

or a salt thereof, with a brominating agent in an acidic reaction medium comprising sulfuric acid to provide a compound corresponding in structure to Formula (II):

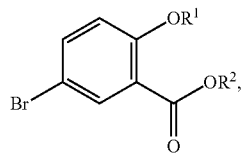

or a salt thereof;

contacting the compound or salt of Formula (II) with a first chlorinating agent without first isolating the compound or salt of Formula (II) from the reaction medium to provide a compound corresponding in structure to Formula (VI):

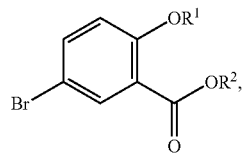

or a salt thereof; and contacting the compound or salt of Formula (VI) with a second chlorinating agent to provide the compound or salt of Formula (III);

wherein:
$R^1$ is hydrogen or $C_{1-6}$-alkyl;
$R^2$ is hydrogen or $C_{1-6}$-alkyl; and
the first chlorinating agent and the second chlorinating agent can be the same or different.

In another aspect, the present disclosure relates to a process for the preparation of a compound corresponding in structure to Formula (III):

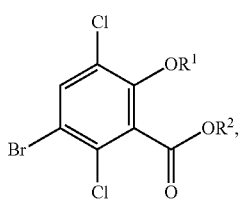

or a salt thereof, the process comprising:

contacting a compound corresponding in structure to Formula (II):

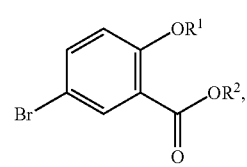

or a salt thereof with a first chlorinating agent without first isolating the compound or salt of Formula (II) from the reaction medium to provide a compound corresponding in structure to Formula (VI):

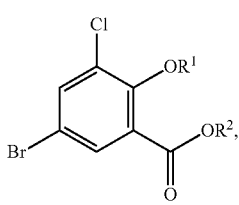
(VI)

or a salt thereof;
modifying the acidic reaction medium to provide an acidic reaction medium comprising oleum after formation of the compound or salt of Formula (VI), and contacting the compound or salt of Formula (VI) with a second chlorinating agent without first isolating the compound or salt of Formula (VI) from the reaction medium to provide the compound of Formula (III); wherein $R^1$ is hydrogen or $C_{1-6}$-alkyl; and $R^2$ is hydrogen or $C_{1-6}$-alkyl; and the first chlorinating agent and the second chlorinating agent can be the same or different.

In another aspect, the present disclosure relates to a process for the preparation of a compound corresponding in structure to Formula (V):

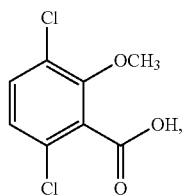
(V)

or a salt thereof, the process comprising:
contacting a compound corresponding in structure to Formula (II):

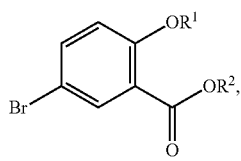
(II)

or a salt thereof, with a chlorinating agent in an acidic reaction medium to provide the compound or salt of Formula (III):

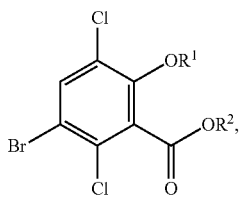
(III)

or a salt thereof;
selectively debrominating the compound or salt of Formula (III) to provide a compound corresponding in structure to Formula (IV):

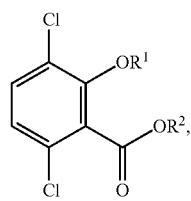
(IV)

or a salt thereof; and
when $R^1$ is other than methyl and/or $R^2$ is other than hydrogen, converting the compound or salt of Formula (IV) to the compound or salt of Formula (V);
wherein $R^1$ is hydrogen or $C_{1-6}$-alkyl; and $R^2$ is hydrogen or $C_{1-6}$-alkyl.

In another aspect, the present disclosure relates to a process for the preparation of a compound corresponding in structure to Formula (V):

(V)

(structure shown)

or a salt thereof, the process comprising:
contacting a compound corresponding in structure to Formula (III-1):

(III-1)

(structure shown)

or a salt thereof, with a methylating agent to provide a compound corresponding in structure to Formula (III-2):

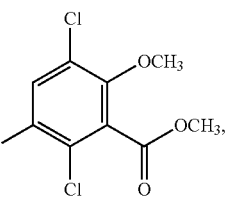
(III-2)

or a salt thereof;
selectively debrominating the compound or salt of Formula (III-2) to provide a compound corresponding in structure to Formula (IV-2):

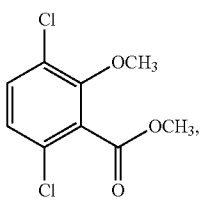
(IV-2)

or a salt thereof; and saponifying the compound or salt of Formula (IV-2) to provide the compound or salt of Formula (V).

In another aspect, the present disclosure relates to a process for the preparation of a compound corresponding in structure to Formula (IV-1):

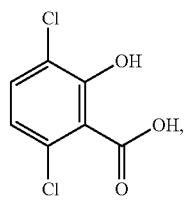
(IV-1)

or a salt thereof, the process comprising contacting a compound corresponding in structure to Formula (X):

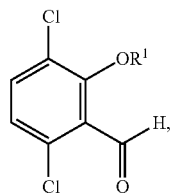
(X)

or a salt thereof, with an oxidizing agent to provide the compound or salt of Formula (VI-1); wherein $R^1$ is hydrogen or $C_{1-6}$-alkyl.

In a another aspect, the present disclosure relates to a process for the preparation of a compound corresponding in structure to Formula (IV-1), or salt thereof, the process comprising contacting a compound corresponding in structure to Formula (VII-1):

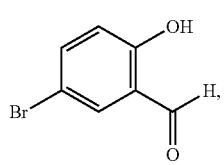
(VII-1)

or a salt thereof, with a first chlorinating agent to provide a compound corresponding in structure to Formula (VIII-1):

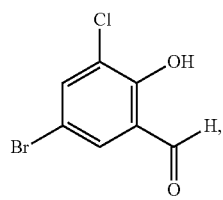
(VIII-1)

or a salt thereof;

contacting the compound or salt of Formula (VIII-1) with a second chlorinating agent to provide a compound corresponding in structure to Formula (IX-1):

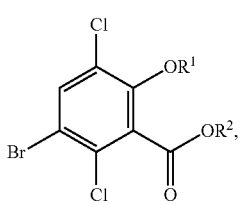
(IX-1)

or a salt thereof;

contacting the compound or salt of Formula (IX-1) with a debrominating agent to provide a compound corresponding in structure to Formula (X-1):

(X-1)

or a salt thereof; thereof; and contacting the compound or salt of Formula (X-1) with an oxidizing agent to provide a compound corresponding in structure to Formula (IV-1), or a salt thereof.

In another aspect, the present disclosure relates to a compound corresponding in structure to Formula (III):

(III)

or a salt thereof, wherein $R^1$ is hydrogen or $C_{1-6}$-alkyl; and $R^2$ is hydrogen or $C_{1-6}$-alkyl.

In another aspect, the present disclosure relates to a compound corresponding in structure to Formula (IX):

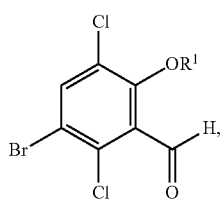

(IX)

or a salt thereof, wherein $R^1$ is hydrogen or $C_{1-6}$-alkyl.

DETAILED DESCRIPTION OF THE INVENTION

This written description uses examples to disclose the invention, including the best mode, and also to enable any person skilled in the art to practice the invention, including making and using any of the disclosed salts, substances, or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. DEFINITIONS

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The abbreviation "BCSA" refers to 5-bromo-3-chlorosalicylic acid (also known as 5-bromo-3-chloro-2-hydroxybenzoic acid).

The abbreviation "BDCSA" refers to 5-bromo-3,6-dichlorosalicylic acid (also known as 3-bromo-2,5-dichloro-6-hydroxybenzoic acid).

The abbreviation "3-Br-SA" refers to 3-bromosalicylic acid (also known as 3-bromo-2-hydroxybenzoic acid).

The abbreviation "5-Br-SA" refers to 5-bromosalicylic acid (also known as 5-bromo-2-hydroxybenzoic acid).

The abbreviation "3,5-Br2-SA" refers to 3,5-dibromosalicylic acid (also known as 3,5-dibromo-2-hydroxybenzoic acid).

The abbreviation "DBCSA" refers to 3,5-dibromo-6-chlorosalicylic acid (also known as 3,5-dibromo-2-chloro-6-hydroxybenzoic acid).

The abbreviation "HCl" refers to hydrochloric acid.

The abbreviation "SA" refers to salicylic acid.

The abbreviation "TCICA" refers to trichloroisocyanuric acid.

II. PREPARATION OF 5-HALO-3,6-DICHLOROSALICYLIC ACID COMPOUNDS (BDCSA PROCESS 1)

In one embodiment, the present disclosure relates, in part, to processes for converting 5-bromosalicylic acid compounds to the corresponding 5-bromo-3,6-dichlorosalicylic acid compounds. The 5-bromo-3,6-dichlorosalicylic acid compounds prepared can be employed as intermediates in the manufacture of dicamba. In particular, the present disclosure relates to processes for converting 5-bromosalicylic acid to 5-bromo-3,6-dichlorosalicylic acid.

In one advantageous embodiment, salicylic acid, a relatively inexpensive and readily available material, is used as a starting material to prepare 5-bromosalicylic acid which is then converted to 5-bromo-3,6-dichlorosalicylic acid. In other embodiments, the 5-bromosalicylic acid can be prepared from a starting material that is an alkylated analog of salicylic acid. Scheme 3 below illustrates one representative route for the preparation of dicamba that begins with a salicylic acid starting material and proceeds through a 5-bromo-3,6-dichlorosalicylic acid intermediate.

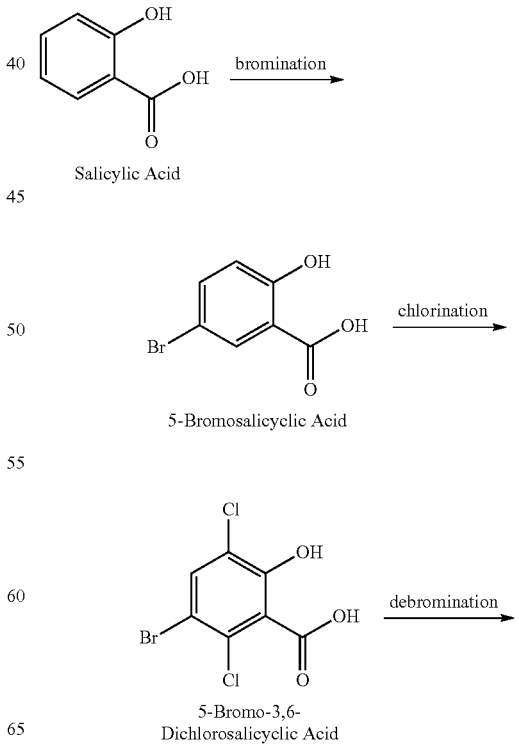

Scheme 3

-continued

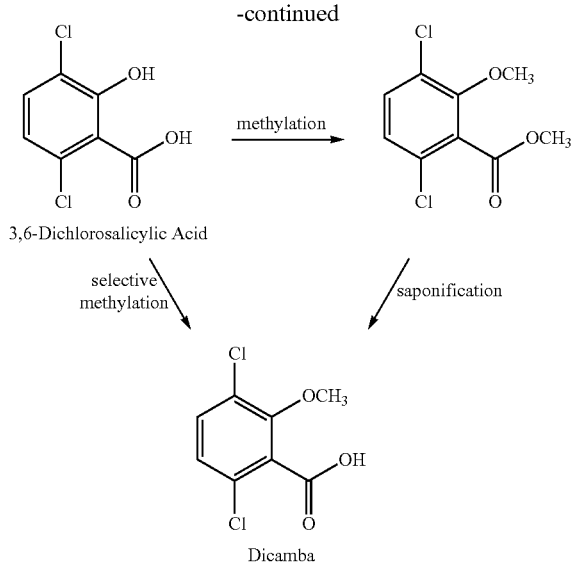

3,6-Dichlorosalicylic Acid methylation → selective methylation ↓  ↗ saponification

Dicamba

Although primarily illustrated throughout this application with 5-bromo-3,6-dichlorosalicylic acid, the processes disclosed in this application can be used to synthesize other 5-bromo-3,6-dichlorosalicylic acid compounds from the corresponding 5-bromosalicylic acid compounds. Accordingly, in one embodiment, the present disclosure relates to a process for the preparation of a compound corresponding in structure to Formula (III):

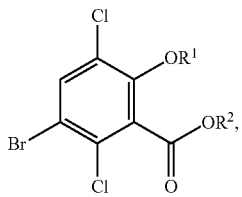

(III)

or a salt thereof, the process comprising:
contacting a compound corresponding in structure to Formula (II):

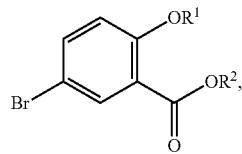

(II)

or a salt thereof, with a chlorinating agent in an acidic reaction medium to provide the compound or salt of Formula (III); wherein $R^1$ is hydrogen or $C_{1-6}$-alkyl; and $R^2$ is hydrogen or $C_{1-6}$-alkyl.

In certain embodiments of the compound or salt of Formula (II) and the compound or salt of Formula (III), $R^1$ is hydrogen, methyl, or ethyl; and $R^2$ is hydrogen, methyl, or ethyl. In another aspect, $R^1$ is hydrogen or methyl; and $R^2$ is hydrogen or methyl. In another aspect, $R^1$ and $R^2$ are each hydrogen (i.e., the compound of Formula (II) is 5-bromosalicylic acid and the compound of Formula (III) is 5-bromo-3,6-dichlorosalicylic acid) and the compounds of Formula (II) and Formula (III) correspond in structures to Formula (II-1) and Formula (III-1), respectively:

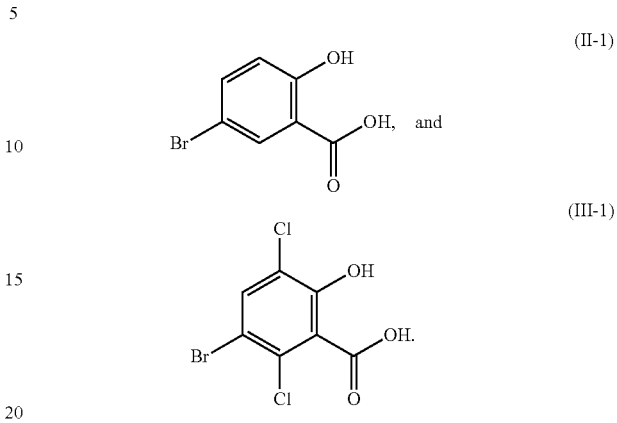

In another aspect, $R^1$ and $R^2$ are each methyl. In another aspect, one of $R^1$ and $R^2$ is hydrogen; and the other of $R^1$ and $R^2$ is methyl.

A. Chlorinating Agent

The chlorinating agent contacted with the compound or salt of Formula (II) generally is a compound that is suitable under the applicable process conditions to effect the chlorination of a compound or salt of Formula (II) in accordance with the disclosed processes. In one embodiment, the chlorinating agent is selected from the group consisting of chlorine gas, trichloroisocyanuric acid, 1,3-dichlorohydantoin, N-chlorosuccinimide, and iodine monochloride. In one aspect, the chlorinating agent is selected from the group consisting of chlorine gas and trichloroisocyanuric acid. In another aspect, the chlorinating agent is trichloroisocyanuric acid. In another aspect, the chlorinating agent is chlorine gas. Use of chlorine gas as the chlorinating agent can be advantageous relative to other chlorinating agent. Among other advantages, chlorine gas is a relatively inexpensive reagent and generally reduces or eliminates the waste by-products that are generated when other chlorinating agents are used (e.g., cyanuric acid is produced when trichloroisocyanuric acid is used as the chlorinating agent).

B. Reaction Medium

The reaction medium generally is an acidic reaction medium that is suitable for the chlorination of the compound or salt of Formula (II) with the chlorinating agent under the applicable process conditions in accordance with the disclosed processes. In one embodiment, the reaction medium comprises one or more acids selected from the group consisting of sulfuric acid, chlorosulfonic acid, and oleum. In one aspect, the reaction medium comprises less than about 5% water by weight. In another aspect, the reaction medium comprises less than about 2% water by weight. In another aspect, the reaction medium is substantially anhydrous. The reaction medium can be prepared in any suitable manner prior to the introduction of the chlorinating agent.

In one embodiment, the reaction medium comprises sulfuric acid. In one aspect, the reaction medium comprises at least about 95% sulfuric acid by weight. In another aspect, the reaction medium comprises at least about 96% sulfuric acid by weight. In another aspect, the reaction medium comprises at least about 97% sulfuric acid by weight. In another aspect, the reaction medium comprises at least about 98% sulfuric acid by weight. In another aspect, the reaction medium comprises at least about 99% sulfuric acid by weight.

In one embodiment, the reaction medium comprises oleum. The reaction medium generally will contain an amount of oleum that is sufficient to maintain the reaction medium in a liquid state under the applicable process conditions. See, e.g., Sections 4.2.2 (page 37) and 12.3.1 (page 113) of Ashar, N. G., A Practical Guide to the Manufacture of Sulfuric Acid, Oleums, and Sulfonating Agents, Springer International Publishing AG (2013).

In one aspect, the reaction medium comprises at least about 5% oleum by weight. In another aspect, the reaction medium comprises at least about 10% oleum by weight. In another aspect, the reaction medium comprises at least about 15% oleum by weight. In another aspect, the reaction medium comprises at least about 20% oleum by weight. In another aspect, the reaction medium comprises at least about 25% oleum by weight. In another aspect, the reaction medium comprises at least about 50% oleum by weight. In another aspect, the reaction medium comprises at least about 60% oleum by weight. In another aspect, the reaction medium comprises from about 5% oleum by weight to about 70% oleum by weight. In another aspect, the reaction medium comprises from about 10% oleum by weight to about 50% oleum by weight. In another aspect, the reaction medium comprises from about 15% oleum by weight to about 40% oleum by weight. In another aspect, the reaction medium comprises from about 20% oleum by weight to about 40% oleum by weight. In another aspect, the reaction medium comprises from about 20% oleum by weight to about 30% oleum by weight. In another aspect, the reaction medium comprises from about 50% oleum by weight to about 80% oleum by weight. In another aspect, the reaction medium comprises from about 60% oleum by weight to about 70% oleum by weight. As illustrated further in this application, the desired oleum concentration in the medium can be achieved, for example, by adding a sufficient amount of sulfur trioxide and/or oleum to a concentrated sulfuric acid medium (e.g., adding a sufficient amount of 65% oleum by weight to a medium containing 95% sulfuric acid by weight to provide a medium containing 25% oleum by weight).

C. Catalyst

In one embodiment, the reaction medium further comprises a catalyst. In one aspect, the catalyst is iodine ($I_2$) or iodine monochloride ("ICl"). In another aspect, the catalyst is iodine. In another aspect, the catalyst is iodine monochloride. Iodine is a solid at room temperature while iodine monochloride is a liquid at room temperature. Since iodine and monochloride iodine provide substantially similar catalytic results in the chlorination reaction, selection between the two catalysts may depend on whether a solid or liquid catalyst is desired.

D. Reaction Stoichiometries

A stoichiometry of 2.0 equivalents of active chlorine in the chlorinating agent is required for the chlorination reaction to convert the compound or salt of Formula (II) to the compound or salt of Formula (III). Although smaller or larger amounts of the chlorinating agent can be employed for the chlorination reaction, a stoichiometric amount or a stoichiometric excess of the active chlorine, for example, at least about 2.0 active chlorine equivalents of chlorinating agent, generally provides a better conversion of the compound or salt of Formula (II) to the compound or salt of Formula (III). When a relatively expensive chlorinating agent such as trichloroisocyanuric acid is used, a stoichiometric excess of the active chlorine is generally more narrowly controlled than in the case of a relatively inexpensive chlorinating agent such as chlorine gas. Accordingly, in one embodiment, the compound or salt of Formula (II) is contacted with about 2.0 to about 8.0 active chlorine equivalents of the chlorinating agent. In one aspect, the compound or salt of Formula (II) is contacted with about 2.0 to about 6.0 active chlorine equivalents of the chlorinating agent. In another aspect, the compound or salt of Formula (II) is contacted with about 2.0 to about 4.0 active chlorine equivalents of the chlorinating agent. In another aspect, the compound or salt of Formula (II) is contacted with about 2.0 to about 3.0 active chlorine equivalents of the chlorinating agent. In another aspect, the compound or salt of Formula (II) is contacted with about 2.0 to about 2.4 active chlorine equivalents of the chlorinating agent. In another aspect, the compound or salt of Formula (II) is contacted with about 2.0 to about 2.2 active chlorine equivalents of the chlorinating agent.

When the chlorinating agent is chlorine gas, the chlorine gas can be introduced into the reaction medium, for example, by means of spargers, bubblers, or the like. In one aspect, the chlorine gas is introduced into the reaction medium at a substantially constant feed rate. In another aspect, the chlorine gas is introduced into the reaction medium at a feed rate and for a period of time sufficient to convert at least about 60% percent of the compound or salt of Formula (II) to the compound or salt of Formula (III). In another aspect, unreacted chlorine gas is recovered overhead and recycled back into the reaction medium. The amount of chlorine gas used during the reaction can be measured by weighing the chlorine gas tank before and after the reaction. In another aspect, the compound or salt of Formula (II) is contacted with at least about 2.0 equivalents of the chlorine gas. Accordingly, in one embodiment, the compound or salt of Formula (II) is contacted with about 2.0 to about 10.0 equivalents of the chlorinating gas. In another embodiment, the compound or salt of Formula (II) is contacted with about 2.0 to about 6.0 equivalents of the chlorine gas. In another embodiment, the compound or salt of Formula (II) is contacted with about 2.0 to about 4.0 equivalents of the chlorine gas.

In some embodiments, the compound or salt of Formula (II) is contacted with the chlorinating agent in the presence of a catalytic amount of a catalyst. In one aspect, the compound or salt of Formula (II) is contacted with the chlorinating agent in the presence of a catalytic amount of iodine or iodine monochloride. In another aspect, the catalytic amount of iodine or iodine monochloride is from about 0.0001 equivalents to about 0.1 equivalents relative to the compound or salt of Formula (II). In another aspect, the catalytic amount of iodine or iodine monochloride is from about 0.0005 equivalents to about 0.1 equivalents relative to the compound or salt of Formula (II). In another aspect, the catalytic amount of iodine or iodine monochloride is from about 0.001 equivalents to about 0.1 equivalents relative to the compound or salt of Formula (II). In another aspect, the catalytic amount of iodine or iodine monochloride is from about 0.005 equivalents to about 0.1 equivalents relative to the compound or salt of Formula (II).

The compound of Formula (II) can be introduced into the reaction medium as a single charge prior to initiation of the chlorination reaction. Alternatively, some or all of the compound of Formula (II) can be introduced into the reaction medium, for example, as a continuous feed stream or in the form of one or more bolus additions over the course of the chlorination reaction. In general, the total amount of the compound or salt of Formula (II) introduced into the reaction medium is from about 0.05 mole to about 4.0 moles of per liter of reaction medium. In one aspect, the total amount of the compound or salt of Formula (II) introduced into the reaction medium is from about 0.1 mole to about 3.0 moles per liter of reaction medium. In another aspect, the total amount of the compound or salt of Formula (II) introduced into the reaction medium is from about 1.0 mole to about 2.5 moles per liter of reaction medium. In another aspect, the total amount of the compound or salt of Formula (II) introduced into the reaction medium is from about 0.1 moles to about 2.0 moles per liter of reaction medium. In another aspect, the total amount of the compound or salt of Formula (II) introduced into the reaction medium is from about 0.4 moles to about 1.5 moles per liter of reaction medium.

In certain embodiments, for example, the concentration of the compound or salt of Formula (II) in a reaction medium comprising oleum (i.e., the payload) can be increased with acceptable results by maintaining an appropriate molar ratio of free sulfur trioxide to the compound or salt of Formula (II). Suitable molar ratios generally will be at least about 4.0 or greater. In one aspect, the reaction medium comprises at least 25% oleum and about 1.5 moles to about 3.0 moles per liter of the compound or salt of Formula (II). In another aspect, the reaction medium comprises at least 25% oleum and about 2.0 moles to about 3.0 moles per liter of the compound or salt of Formula (II). In another aspect, the reaction medium comprises at least 25% oleum and about 2.25 moles per liter of the compound or salt of Formula (II). When the concentration of the compound or salt of Formula (II) is increased, the overall volume of sulfuric acid and oleum needed for the reaction is reduced in a corresponding manner which can be a potential advantage in large-scale manufacturing and also result in cost savings. In addition, the higher concentrations of the compound or salt of Formula (II) in these embodiments also appear to allow for a reduction in the amount of catalyst required relative to embodiments where the reaction medium comprises about 20% oleum and about 1.5 moles moles per liter of the compound or salt of Formula (II).

E. Reaction Conditions

In general, the reaction medium is maintained at a temperature from about 0° C. to about 100° C. during the contacting step. In one aspect, the reaction medium is maintained at a temperature from about 0° C. to about 60° C. during the contacting step. In another aspect, the reaction medium is maintained at a temperature from about 5° C. to about 35° C. during the contacting step.

The improved processes of the present disclosure provide a suitable conversion of the compound or salt of Formula (II) to the compound or salt of Formula (III). In one embodiment, the percent conversion of the compound or salt of Formula (II) to the compound or salt of Formula (III) is at least about 60%. In one aspect, the percent conversion of the compound or salt of Formula (II) to the compound or salt of Formula (III) is at least about 65%. In another aspect, the percent conversion of the compound or salt of Formula (II) to the compound or salt of Formula (III) is at least about 70%.

F. Illustrative Embodiment: Chlorine Gas

In one representative embodiment, the present disclosure relates to a process for the preparation of a compound corresponding in structure to Formula (III-1):

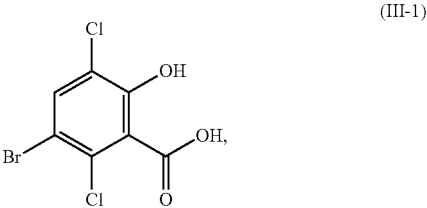 [SMILES: O=C(O)c1c(O)c(Cl)cc(Br)c1Cl]

or a salt thereof, the process comprising:
contacting a compound corresponding in structure to Formula (II-1):

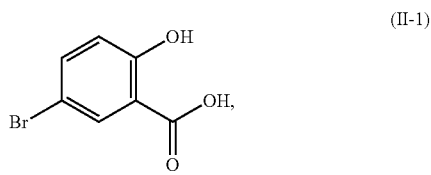

or a salt thereof, with chlorine gas in an acidic reaction medium comprising oleum to provide the compound or salt of Formula (III-1) $R^1$ is hydrogen; and $R^2$ is hydrogen in the compounds of Formula (II) and Formula (III)).

In another embodiment:
the total amount of the compound or salt of Formula (II-1) introduced into the reaction medium is from about 0.05 mole to about 4.0 moles of per liter of reaction medium;
the compound or salt of Formula (II-1) is contacted with at least about 2.0 equivalents of chlorine gas; and
the reaction medium comprises from about 5% oleum by weight to about 70% oleum by weight.

In another embodiment:
the total amount of the compound or salt of Formula (II-1) introduced into the reaction medium is from about 0.1 mole to about 3.0 moles per liter of reaction medium;
the compound or salt of Formula (II-1) is contacted with at least about 2.0 equivalents of chlorine gas; and
the reaction medium comprises from about 10% oleum by weight to about 70% oleum by weight.

In another embodiment:
the total amount of the compound or salt of Formula (II-1) introduced into the reaction medium is from about 1.0 mole to about 2.5 moles per liter of reaction medium;
the compound or salt of Formula (II-1) is contacted with at least about 2.0 equivalents of chlorine gas; and
the reaction medium comprises from about 15% oleum by weight to about 40% oleum by weight.

In another embodiment:
the total amount of the compound or salt of Formula (II-1) introduced into the reaction medium is from about 0.1 moles to about 2.0 moles per liter of reaction medium;

the compound or salt of Formula (II-1) is contacted with at least about 2.0 equivalents of chlorine gas; and the reaction medium comprises from about 20% oleum by weight to about 40% oleum by weight.

In another embodiment:

the total amount of the compound or salt of Formula (II-1) introduced into the reaction medium is from about 0.4 moles to about 1.5 moles per liter of reaction medium;

the compound or salt of Formula (II-1) is contacted with at least about 2.0 equivalents of chlorine gas; and the reaction medium comprises from about 20% oleum by weight to about 30% oleum by weight.

In another embodiment:

the total amount of the compound or salt of Formula (II-1) introduced into the reaction medium is from about 1.5 mole to about 3.0 moles per liter of reaction medium;

the compound or salt of Formula (II-1) is contacted with at least about 2.0 equivalents of chlorine gas; and the reaction medium comprises from about 25% oleum by weight to about 80% oleum by weight.

In another embodiment:

the total amount of the compound or salt of Formula (II-1) introduced into the reaction medium is from about 2.0 mole to about 3.0 moles per liter of reaction medium;

the compound or salt of Formula (II-1) is contacted with at least about 2.0 equivalents of chlorine gas; and the reaction medium comprises from about 25% oleum by weight to about 40% oleum by weight.

In each of the above embodiments, the equivalent of the chlorine gas can be controlled by recovering the unreacted chlorine gas overhead and recycling back into the reaction medium. Accordingly, in one embodiment, the compound or salt of Formula (II-1) is contacted with about 2.0 to about 10.0 equivalents of the chlorinating gas. In another embodiment, the compound or salt of Formula (II-1) is contacted with about 2.0 to about 6.0 equivalents of the chlorine gas. In another embodiment, the compound or salt of Formula (II-1) is contacted with about 2.0 to about 4.0 equivalents of the chlorine gas.

In each of the above embodiments, the reaction medium may further comprise a catalyst such as iodine or iodine monochloride. In one aspect, the compound or salt of Formula (II-1) is contacted with chlorine gas in the presence of about 0.0001 equivalents to about 0.1 equivalents of iodine relative to the compound or salt of Formula (II-1). In another aspect, the compound or salt of Formula (II-1) is contacted with chlorine gas in the presence of about 0.0005 equivalents to about 0.1 equivalents relative to the compound or salt of Formula (II-1). In another aspect, the compound or salt of Formula (II-1) is contacted with chlorine gas in the presence of about 0.001 equivalents to about 0.1 equivalents of iodine relative to the compound or salt of Formula (II-1). In another aspect, the compound or salt of Formula (II-1) is contacted with chlorine gas in the presence of about 0.005 equivalents to about 0.1 equivalents of iodine relative to the compound or salt of Formula (II-1).

G. Illustrative Embodiment: Trichloroisocyuranic Acid

In one representative embodiment, the present disclosure relates to a process for the preparation of a compound corresponding in structure to Formula (III-1):

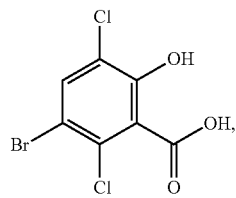

or a salt thereof, the process comprising:

contacting a compound corresponding in structure to Formula (II-1):

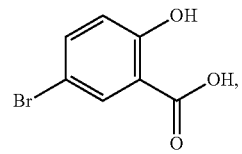

or a salt thereof, with trichloroisocyanuric acid in an acidic reaction medium comprising oleum to provide the compound or salt of Formula (III-1) $R^1$ is hydrogen; and $R^2$ is hydrogen in the compounds of Formula (II) and Formula (III)).

One trichloroisocyanuric acid molecule can provide up to three active chlorine species (e.g., $Cl^+$) in the chlorination reaction. The equivalents described herein are the active chlorine equivalents of trichloroisocyanuric acid (i.e., 1.0 equivalent of trichloroisocyanuric acid equals to about 3.0 active chlorine equivalents).

Accordingly, in another embodiment:

the total amount of amount of the compound or salt of Formula (II-1) introduced into the reaction medium is from about 0.05 mole to about 4.0 moles of per liter of reaction medium;

the compound or salt of Formula (II-1) is contacted with about 2.0 to about 8.0 active chlorine equivalents of trichloroisocyanuric acid; and the reaction medium comprises from about 5% oleum by weight to about 70% oleum by weight.

In another embodiment:

the total amount of amount of the compound or salt of Formula (II-1) introduced into the reaction medium is from about 0.1 mole to about 3.0 moles per liter of reaction medium;

the compound or salt of Formula (II-1) is contacted with about 2.0 to about 6.0 active chlorine equivalents of trichloroisocyanuric acid; and the reaction medium comprises from about 10% oleum by weight to about 70% oleum by weight.

In another embodiment:

the total amount of compound or salt of Formula (II-1) introduced into the reaction medium is from about 1.0 mole to about 2.5 moles per liter of reaction medium;

the compound or salt of Formula (II-1) is contacted with about 2.0 to about 4.0 active chlorine equivalents of trichloroisocyanuric acid; and the reaction medium comprises from about 15% oleum by weight to about 40% oleum by weight.

In another embodiment:

the total amount of the compound or salt of Formula (II-1) introduced into the reaction medium is from about 0.1 moles to about 2.0 moles per liter of reaction medium;

the compound or salt of Formula (II-1) is contacted with about 2.0 to about 3.0 active chlorine equivalents of trichloroisocyanuric acid; and the reaction medium comprises from about 20% oleum by weight to about 40% oleum by weight.

In another embodiment:

the total amount of the compound or salt of Formula (II-1) introduced into the reaction medium is from about 0.4 moles to about 1.5 moles per liter of reaction medium;

the compound or salt of Formula (II-1) is contacted with about 2.0 to about 2.4 active chlorine equivalents of trichloroisocyanuric acid; and the reaction medium comprises from about 20% oleum by weight to about 30% oleum by weight.

In another embodiment:

the total amount of the compound or salt of Formula (II-1) introduced into the reaction medium is from about 1.5 mole to about 3.0 moles per liter of reaction medium;

the compound or salt of Formula (II-1) is contacted with about 2.0 to about 4.0 active chlorine equivalents of trichloroisocyanuric acid; and the reaction medium comprises from about 25% oleum by weight to about 80% oleum by weight.

In another embodiment:

the total amount of the compound or salt of Formula (II-1) introduced into the reaction medium is from about 2.0 mole to about 3.0 moles per liter of reaction medium;

the compound or salt of Formula (II-1) is contacted with about 2.0 to about 4.0 active chlorine equivalents of trichloroisocyanuric acid; and the reaction medium comprises from about 25% oleum by weight to about 40% oleum by weight.

In each of the above embodiments, the reaction medium may further comprise a catalyst such as iodine or iodine monochloride. In one aspect, the compound or salt of Formula (II-1) is contacted with trichloroisocyanuric acid in the presence of about 0.0001 equivalents to about 0.1 equivalents of iodine relative to the compound or salt of Formula (II-1). In another aspect, the compound or salt of Formula (II-1) is contacted with trichloroisocyanuric acid in the presence of about 0.0005 equivalents to about 0.1 equivalents relative to the compound or salt of Formula (II-1). In another aspect, the compound or salt of Formula (II-1) is contacted with trichloroisocyanuric acid in the presence of about 0.001 equivalents to about 0.1 equivalents of iodine relative to the compound or salt of Formula (II-1). In another aspect, the compound or salt of Formula (II-1) is contacted with trichloroisocyanuric acid in the presence of about 0.005 equivalents to about 0.1 equivalents of iodine relative to the compound or salt of Formula (II-1).

III. PREPARATION OF 5-BROMOSALICYLIC ACID COMPOUNDS

The compound or salt of Formula (II) employed in the above-described processes can be prepared by any suitable method. In one embodiment, the compound or salt of Formula (II) is prepared by brominating a compound corresponding in structure to Formula (I):

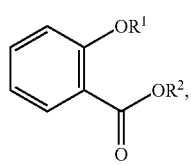

(I)

or a salt thereof, to provide the compound of Formula (II):

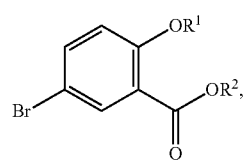

(II)

or a salt thereof; wherein $R^1$ is hydrogen or $C_{1-6}$-alkyl; and $R^2$ is hydrogen or $C_{1-6}$-alkyl.

In certain embodiments of the compound or salt of Formula (I) and the compound or salt of Formula (II), $R^1$ is hydrogen, methyl, or ethyl; and $R^2$ is hydrogen, methyl, or ethyl. In another aspect, $R^1$ and $R^2$ are each hydrogen (i.e., the compound of Formula (I) is salicylic acid and the compound of Formula (II) is 5-bromosalicylic acid) and the compound of Formula (II) corresponds in structure to Formula (II-1):

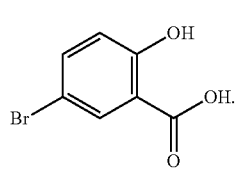

(II-1)

In another aspect, $R^1$ is $R^1$ and $R^2$ are each methyl. In another aspect, one of $R^1$ and $R^2$ is hydrogen; and the other of $R^1$ and $R^2$ is methyl.

The brominating step can be carried out in any suitable manner such as, for example, contacting the compound or salt of Formula (I) with bromine (Br$_2$), hydrogen bromide (HBr), or an alkali metal halide (such as an alkali metal bromide) in a reaction medium comprising sulfuric acid to provide the compound or salt of Formula (II). In one embodiment, the compound or salt of Formula (I) is contacted with bromine (Br$_2$). In another embodiment, the compound or salt of Formula (I) is contacted with hydrogen bromide (HBr). In another embodiment, the compound or salt of Formula (I) is contacted with an alkali metal halide. In another embodiment, the alkali metal halide is sodium bromide. The preparation of 5-bromosalicylic acid from salicylic acid has been reported, for example, in Hussey, Allen S. et al., "The Reaction of Magnesium with 2,4-Dibromoanisole," J. Am. Chem. Soc., 72(2): 830-832 (1950); and Adibi, Hadi et al., "A convenient and regioselective oxidative bromination of electron-rich aromatic rings using potassium bromide and benzyltriphenylphosphonium peroxymonosulfate under nearly neutral reaction conditions," Tetrahedron Lett. 48: 1255-1259 (2007).

In one embodiment, the brominating step is conducted in a reaction medium comprising an acid selected from the group consisting of sulfuric acid, oleum, and acetic acid. In one aspect, the reaction medium comprises sulfuric acid. In another aspect, the reaction medium comprises at least about 95% sulfuric acid by weight. In another aspect, the reaction medium comprises at least about 98% sulfuric acid by weight. In another aspect, the reaction medium comprises oleum. In another aspect, the reaction medium comprises sulfuric acid and acetic acid. In another aspect, the reaction medium comprises oleum and acetic acid.

IV. ALTERNATIVE PROCESS FOR THE PREPARATION OF 5-BROMO-3,6-DICHLOROSALICYLIC ACID COMPOUNDS (BDCSA PROCESS 2)

The present disclosure further relates to an alternative process ("BDCSA Process 2") for preparing a 5-bromo-3,6-dichlorosalicylic acid compound. This alternative process differs, in part, from the previously described process (BDCSA Process 1) in that the salicylic acid compound starting material is brominated and monochlorinated in the same reaction vessel to provide a 5-bromo-3-chlorosalicylic acid compound without first isolating the brominated intermediate. The resulting 5-bromo-3-chlorosalicylic acid compound is then further chlorinated to provide the 5-bromo-3,6-dichlorosalicylic acid compound. The 5-bromo-3-chlorosalicylic acid compound can be isolated and then further chlorinated to provide the 5-bromo-3,6-dichlorosalicylic acid compound or, alternatively, the reaction vessel medium can be modified to provide conditions suitable for the further chlorination of the 5-bromo-3-chlorosalicylic acid compound as part of a "one-pot" process.

Although BDCSA Process 1 provides an acceptable overall yield of 5-bromo-3,6-dichlorosalicylic acid, BDCSA Process 2 likewise provides an acceptable overall yield and additionally may provide processing advantages in larger-scale manufacturing operations. BDCSA Process 1 as conducted on a smaller scale generally has involved pouring the crude reaction mixture into ice water to quench the bromination reaction and then isolating the 5-bromosalicylic acid by organic extraction for use in the subsequent chlorination reaction. Such an aqueous workup procedure, however, can present a number of processing challenges for larger-scale manufacturing including: (a) a large quantity of chilled water (typically at least a 10-fold excess) is required for quenching, (b) the quench reaction is very exothermic, (c) sulfonylation of the 5-bromosalicylic acid at the 3-position can occur if the temperature during quenching is not properly controlled and becomes too hot, (d) the resulting aqueous sulfuric acid solution is corrosive and can adversely affect piping and equipment coming into contact with the mixture, and (e) the 5-bromosalicylic acid must be dried and substantially anhydrous for use in the subsequent chlorination step (which can add to cost and technical challenges). Further, sulfonylation of the isolated 5-bromosalicylic acid at the 3-position can occur during the subsequent chlorination step. When the acidic reaction medium comprises oleum, for example, sulfonylation competes to some extent with chlorination at the electron-rich 3-position of the ring.

In contrast, BDCSA Process 2 generally comprises: (a) brominating the salicylic acid compound starting material to provide a reaction mixture comprising a 5-bromosalicylic acid compound, (b) chlorinating the 5-bromosalicylic acid compound to provide a 5-bromo-3-chlorosalicylic acid compound without first isolating the 5-bromosalicylic acid compound from the reaction mixture, and (c) further chlorinating the 5-bromo-3-chlorosalicylic acid compound to provide the 5-bromo-3,6-dichlorosalicylic acid compound. Proper control of the reaction conditions effectively reduces the impact of the competing sulfonylation reaction and other processing challenges. For example, bromination and monochlorination of the salicylic acid compound starting material can be carried out in an acidic reaction medium comprising sulfuric acid to provide the 5-bromo-3-chlorosalicylic acid compound. The resulting 5-bromo-3-chlorosalicylic acid compound can either be isolated and then further chlorinated or chlorinated in situ to provide the 5-bromo-3,6-dichlorosalicylic acid compound. During the monochlorination of 5-bromosalicylic acid, the resulting 5-bromo-3-chlorosalicylic acid compound precipitates in the acidic reaction medium comprising sulfuric acid (e.g., the concentrated sulfuric acid of about 96% sulfuric acid by weight). Therefore, the 5-bromo-3-chlorosalicylic acid compound can be isolated as a solid by filtration from the acidic reaction medium. If a "one-pot" process is desired, the reaction medium comprising the 5-bromo-3-chlorosalicylic acid compound can be modified to provide an acidic reaction medium comprising oleum in which the 5-bromo-3-chlorosalicylic acid compound is further chlorinated to provide the 5-bromo-3,6-dichlorosalicylic acid compound. Any suitable means can be employed to convert the initial acidic reaction medium into an acidic reaction medium comprising oleum, for example, by adding a sufficient quantity of sulfur trioxide and/or oleum to the reaction medium (e.g., adding a sufficient quantity of 65% oleum to 95% sulfuric acid to yield an acidic reaction medium comprising 20%, 25%, or other suitable concentrations of oleum).

Accordingly, in one embodiment, the present disclosure relates to a process for the preparation of a compound corresponding in structure to Formula (VI):

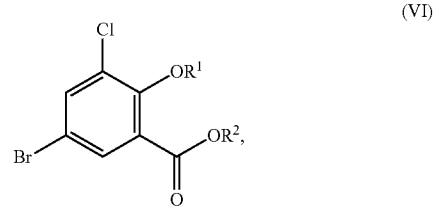

or a salt thereof, the process comprising:

contacting a compound corresponding in structure to Formula (I):

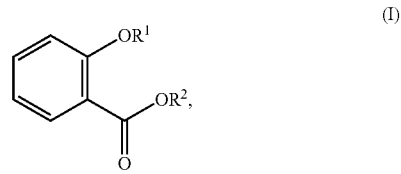

or a salt thereof, with a brominating agent in an acidic reaction medium to provide a compound corresponding in structure to Formula (II):

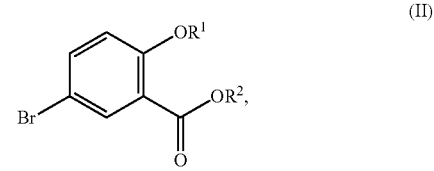

or a salt thereof; and contacting the compound or salt of Formula (II) with a chlorinating agent to provide the compound or salt of Formula (VI);

wherein:

$R^1$ is hydrogen or $C_{1-6}$-alkyl; and $R^2$ is hydrogen or $C_{1-6}$-alkyl.

In one aspect, the compound or salt of Formula (II) is contacted with the chlorinating agent without first isolating the compound or salt of Formula (II) from the reaction medium to provide the compound or salt of Formula (VI). In another aspect, the compound or salt of Formula (II) is isolated from the reaction mixture and then contacted with the chlorinating agent to provide the compound or salt of Formula (VI).

In another embodiment, the present disclosure relates to a process for the preparation of a compound corresponding in structure to Formula (III):

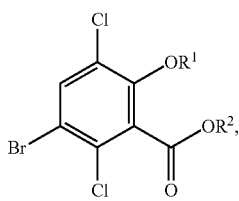

(III)

or a salt thereof, the process comprising:

contacting a compound corresponding in structure to Formula (VI):

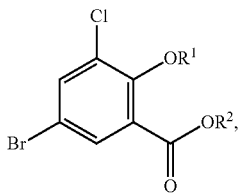

(VI)

or a salt thereof, with a chlorinating agent in an acidic reaction medium comprising oleum to provide the compound or salt of Formula (III):

wherein:

$R^1$ is hydrogen or $C_{1-6}$-alkyl; and $R^2$ is hydrogen or $C_{1-6}$-alkyl.

In another embodiment, the present disclosure relates to a process for the preparation of a compound corresponding in structure to Formula (III):

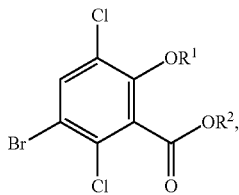

(III)

or a salt thereof, the process comprising:

contacting a compound corresponding in structure to Formula (I):

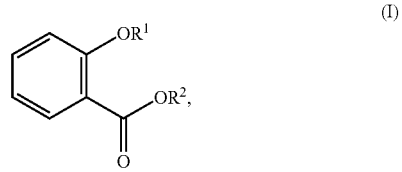

(I)

or a salt thereof, with a brominating agent in an acidic reaction medium comprising sulfuric acid to provide a compound corresponding in structure to Formula (II):

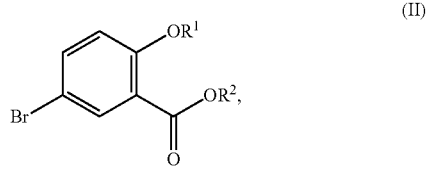

(II)

or a salt thereof;

contacting the compound or salt of Formula (II) with a first chlorinating agent without first isolating the compound or salt of Formula (II) from the reaction medium to provide a compound corresponding in structure to Formula (VI):

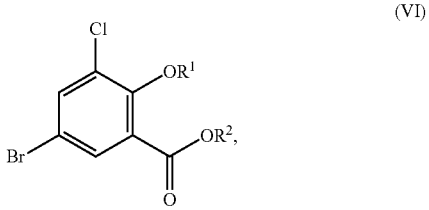 [SMILES: O=C(O)c1cc(Br)cc(Cl)c1O]

(VI)

or a salt thereof; and contacting the compound or salt of Formula (VI) with a second chlorinating agent to provide the compound or salt of Formula (III);

wherein:

$R^1$ is hydrogen or $C_{1-6}$-alkyl;

$R^2$ is hydrogen or $C_{1-6}$-alkyl; and the first chlorinating agent and the second chlorinating agent can be the same or different.

In one aspect, the compound or salt of Formula (VI) is contacted with the second chlorinating agent without first isolating the compound or salt of Formula (VI) from the reaction medium to provide the compound or salt of Formula (III). In another aspect, the compound or salt of Formula (VI) is isolated from the reaction medium and subsequently contacted with the second chlorinating agent to provide the compound or salt of Formula (III).

In another embodiment, the present disclosure relates to a process for the preparation of a compound corresponding in structure to Formula (III):

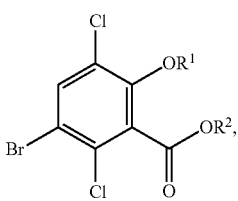

or a salt thereof, the process comprising:
contacting a compound corresponding in structure to Formula (I):

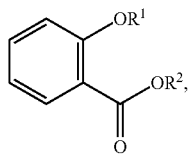

or a salt thereof, with a brominating agent in an acidic reaction medium comprising sulfuric acid to provide a compound corresponding in structure to Formula (II):

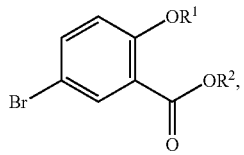

or a salt thereof;
contacting the compound or salt of Formula (II) with a first chlorinating agent without first isolating the compound or salt of Formula (II) from the reaction medium to provide a compound corresponding in structure to Formula (VI):

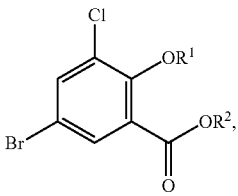

or a salt thereof;
modifying the acidic reaction medium to provide an acidic reaction medium comprising oleum after formation of the compound or salt of Formula (VI), and contacting the compound or salt of Formula (VI) with a second chlorinating agent without first isolating the compound or salt of Formula (VI) from the reaction medium to provide the compound of Formula (III);
wherein:
$R^1$ is hydrogen or $C_{1-6}$-alkyl;
$R^2$ is hydrogen or $C_{1-6}$-alkyl; and
the first chlorinating agent and the second chlorinating agent can be the same or different.

In certain embodiments of the above-described processes relating to the compounds or salts of Formula (I), Formula (II), Formula (III), and Formula (VI), $R^1$ is hydrogen, methyl, or ethyl; and $R^2$ is hydrogen, methyl, or ethyl. In one aspect, $R^1$ is hydrogen or methyl; and $R^2$ is hydrogen or methyl. In another aspect, $R^1$ and $R^2$ are each methyl. In another aspect, one of $R^1$ and $R^2$ is hydrogen and the other of $R^1$ and $R^2$ is methyl. In another aspect, $R^1$ and $R^2$ are each hydrogen and the compounds of Formula (I), Formula (II), Formula (VI), and Formula (III) correspond in structures to Formula (I-1), Formula (II-1), Formula (VI-1), and Formula (III-1), respectively:

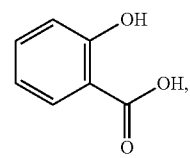

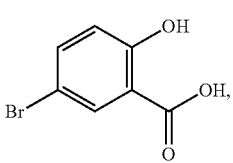

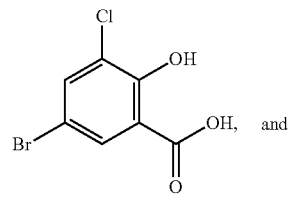

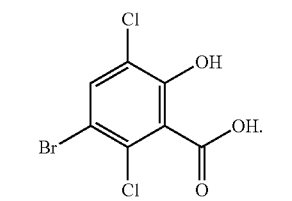

In some illustrative embodiments, 5-bromo-3,6-dichlorosalicylic acid is prepared from salicylic acid in accordance with BDCSA Process 2 with or without isolating 5-bromo-3-chlorosalicylic acid, as illustrated in Scheme 4 below:

Scheme 4

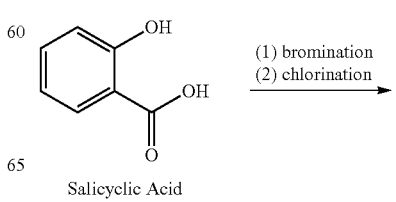

Salicyclic Acid

-continued

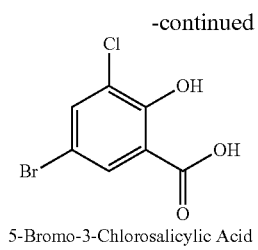
5-Bromo-3-Chlorosalicylic Acid chlorination

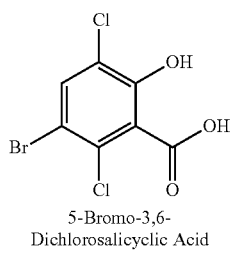
5-Bromo-3,6-Dichlorosalicyclic Acid

Salicylic acid is contacted with bromine in a concentrated sulfuric acid (e.g., 98% sulfuric acid) reaction medium to provide 5-bromosalicylic acid. The resulting 5-bromosalicylic acid, which is not isolated from the reaction medium, is then chlorinated to provide 5-bromo-3-chlorosalicylic acid (e.g., by bubbling chlorine gas into the concentrated sulfuric acid medium). In one embodiment, the 5-bromo-3-chlorosalicylic acid compound is isolated by filtration from the concentrated sulfuric acid reaction medium. The solid of 5-bromo-3-chlorosalicylic acid is then placed in the sulfuric acid reaction medium comprising oleum (e.g., a 20% oleum solution). In another embodiment, the concentrated sulfuric acid medium comprising the 5-bromo-3-chlorosalicylic acid is then converted into a reaction medium comprising oleum (e.g., by bubbling sulfur trioxide into the concentrated sulfuric acid medium or adding an oleum solution to the concentrated sulfuric acid medium to provide the desired oleum medium (e.g., adding a sufficient amount of a 65% oleum solution to the concentrated sulfuric acid medium to yield a 20% oleum medium). The 5-bromo-3-chlorosalicylic acid is then chlorinated to provide 5-bromo-3,6-dichlorosalicylic acid (e.g., by bubbling chlorine gas into the oleum medium in the presence of a suitable catalyst such as iodine). As the electron rich 3- and 5-positions of 5-bromo-3-chlorosalicylic acid are already substituted, exposure to sulfur trioxide should not result in significant sulfonylation of the 5-bromo-3-chlorosalicylic acid.

In general, the bromination and chlorination conditions for BDCSA Process 2 are as previously described for the BDCSA Process 1 except as otherwise stated. For example, the chlorination stoichiometries are appropriately adjusted for each chlorination reaction (i.e., reduced by about 50% for the 3-position chlorination reaction and about 50% for the 6-position chlorination reaction).

The resulting 5-bromo-3,6-dichlorosalicylic acid can be isolated from the reaction mixture and, if desired, purified using conventional techniques. Generally, a portion of the 5-bromo-3,6-dichlorosalicylic acid will precipitate out of the oleum medium during the chlorination reaction. It has been discovered, however, that diluting the oleum medium to provide a sulfuric acid solution once the chlorination reaction is complete (e.g., by diluting the reaction medium comprising oleum with, e.g., a sufficient quantity of a 50% to 95% sulfuric acid solution) can be advantageous as it results in additional precipitation of the 5-bromo-3,6-dichlorosalicylic acid. Alternatively, the 5-bromo-3,6-dichlorosalicylic acid can be directly filtered from the oleum medium.

The filtered solid of 5-bromo-3,6-dichlorosalicylic acid can be further washed with a concentrated sulfuric acid followed by water, and subsequently dried. The direct filtration can be advantageous as it reduces the usage of the sulfuric acid solution in the aforementioned diluting method. Other isolation techniques can be employed, however, such as distilling the reaction medium to remove oleum and/or chlorosulfonic acid thereby promoting precipitation of the 5-bromo-3,6-dichlorosalicylic acid.

V. PREPARATION OF 3,6-DICHLOROSALICYLIC ACID COMPOUNDS

The compounds and salts of Formula (III) can be selectively debrominated to provide the corresponding 3,6-dichlorosalicylic acid compounds (such as 3,6-dichlorosalicylic acid) which can be employed as intermediates in the manufacture of dicamba. Accordingly, the previously described processes may further comprise selectively debrominating the compound or salt of Formula (III):

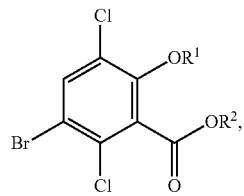
(III)

to provide a compound corresponding in structure to Formula (IV):

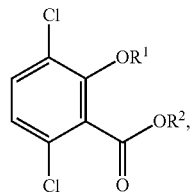
(IV)

or a salt thereof; wherein $R^1$ is hydrogen or $C_{1-6}$-alkyl; and $R^2$ is hydrogen or $C_{1-6}$-alkyl.

In certain embodiments of the compound or salt of Formula (III) and the compound or salt of Formula (IV), $R^1$ is hydrogen, methyl, or ethyl; and $R^2$ is hydrogen, methyl, or ethyl. In another aspect, $R^1$ and $R^2$ are each hydrogen (i.e., the compound of Formula (III) is 5-bromo-3,6-dichlorosalicylic acid and the compound of Formula (IV) is 3,6-dichlorosalicylic acid) and the compound of Formula (III) and Formula (IV) corresponds in structures to Formula (III-1) and Formula (IV-1):

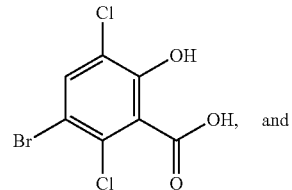
(III-1)

and

-continued

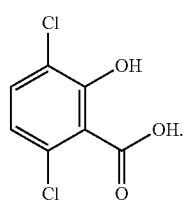

(IV-1)

In another aspect, $R^1$ and $R^2$ are each methyl (i.e., the compound of Formula (III) is methyl 3-bromo-2,5-dichloro-6-methoxybenzoate and the compound of Formula (IV) is methyl 2,5-dichloro-6-methoxybenzoate) and the compound of Formula (III) and Formula (IV) corresponds in structures to Formula (III-2) and Formula (IV-2):

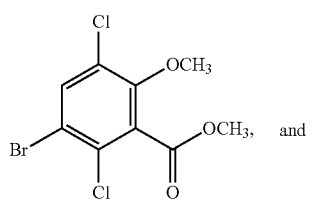

(III-2)

and

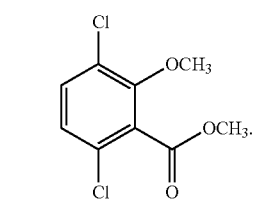

(IV-2)

In another aspect, one of $R^1$ and $R^2$ is hydrogen; and the other of $R^1$ and $R^2$ is methyl.

The debrominating step can be carried out in any suitable manner such as, for example, catalytically hydrogenolyzing the compound or salt of Formula (III) to generate the compound or salt of Formula (IV). In one aspect, the compound or salt of Formula (III) is contacted with hydrogen in the presence of a suitable catalyst to generate the compound or salt of Formula (IV). In another aspect, the catalyst is selected from the group consisting of palladium catalysts and platinum catalysts. In another aspect, the catalyst is a palladium catalyst. In another aspect, the catalyst is a platinum catalyst.

The debrominating step can be conducted in any suitable solvent or combination of solvents. In general, the debrominating step will be conducted in a nonpolar solvent or combination of solvents. In one aspect, the solvent or combination of solvents comprises one or more members of the group consisting of alkanoic acids, carboxylate esters, and aqueous sulfuric acid. In another embodiment, the solvent or combination of solvents comprises one or more members of the group consisting of acetic acid and ethyl acetate.

In one embodiment, the debrominating step comprises contacting the compound or salt of Formula (III) with a catalyst in the presence of a base in a reaction medium comprising a nonpolar solvent. In one aspect, the base is an alkali metal alkanoate. Additional, nonlimiting examples of suitable debrominating conditions are illustrated in Table 10-A of Example 10.

Without being bound to a particular theory, in some embodiments, impurities (e.g., iodine-containing species) in the 5-bromo-3,6-dichlorosalicylic acid compound are believed to poison the catalyst; therefore they can affect the efficiency of dehalogenation. Generally, such impurities can be removed by suspending the yellow-orange colored solid of 5-bromo-3,6-dichlorosalicylic acid in an organic solvent, for example, xylenes. The resulting filtered solid of 5-bromo-3,6-dichlorosalicylic acid can be substantially free of color and undergo debrominating in the next step effectively. It has been discovered, however, that the 5-bromo-3,6-dichlorosalicylic acid compound obtained from the previous described direct filtration method (i.e., direct filtration from the oleum medium) can be used directly for the dehalogenation step without further process.

VII. SELECTIVE CHLORINATION AND DEBROMINATION OF 5-BROMO-2-HYDROXYBENZALDEHYDE COMPOUNDS

The present disclosure further relates to an alternative process for preparing 3,6-dichlorosalicylic acid compounds from 5-bromo-2-hydroxybenzaldehyde compounds as illustrated in Scheme 5 below:

Scheme 5

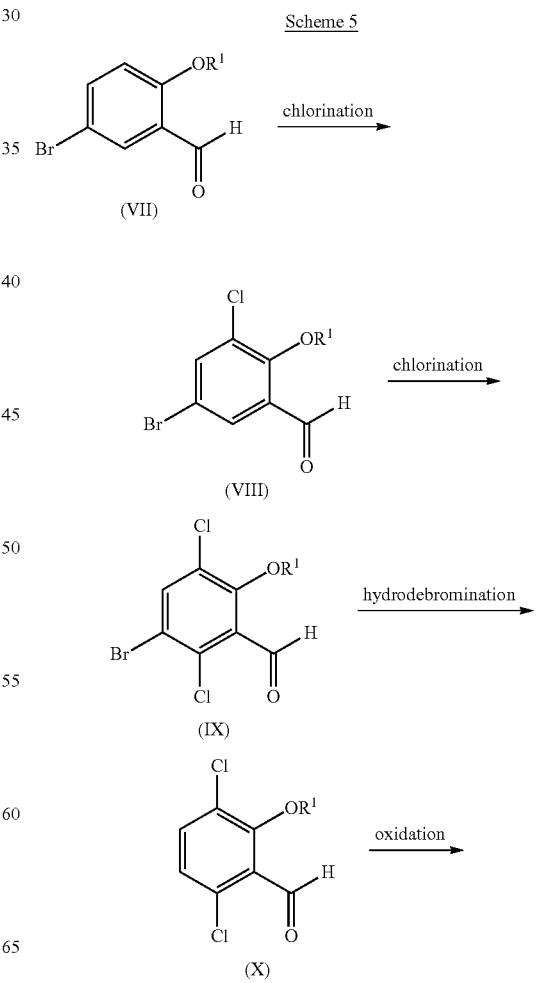

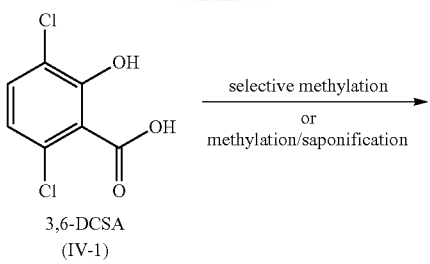

3,6-DCSA
(IV-1)

selective methylation
or
methylation/saponification

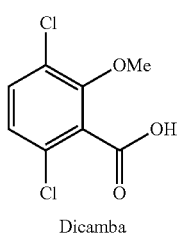

Dicamba

In particular, the present disclosure relates to processes for selectively preparing 3,6-dichlorosalicylic acid from 5-bromo-2-hydroxybenzaldehyde, i.e., the compounds of Scheme 5 wherein $R^1$ is hydrogen.

Accordingly, in one embodiment, the present disclosure relates to a process for the preparation of a compound corresponding in structure to Formula (VIII):

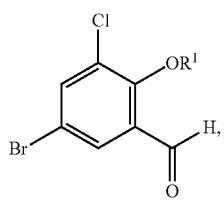
(VIII)

or a salt thereof, the process comprising:
contacting a compound corresponding in structure to Formula (VII):

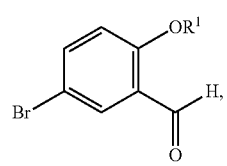
(VII)

or a salt thereof, with a chlorinating agent to provide the compound or salt of Formula (VIII);
wherein $R^1$ is hydrogen or $C_{1-6}$-alkyl.

In another embodiment, the present disclosure relates to a process for the preparation of a compound corresponding in structure to Formula (IX):

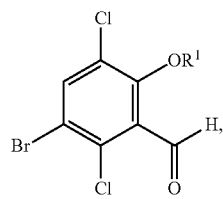
(IX)

or a salt thereof, the process comprising:
contacting a compound corresponding in structure to Formula (VIII):

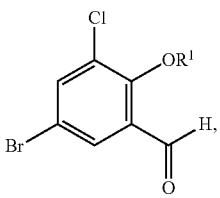
(VIII)

or a salt thereof, with a chlorinating agent to provide the compound or salt of Formula (IX);
wherein $R^1$ is hydrogen or $C_{1-6}$-alkyl.

In another embodiment, the present disclosure relates to a process for the preparation of a compound corresponding in structure to Formula (X):

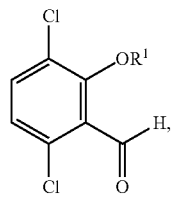
(X)

or a salt thereof, the process comprising:
contacting a compound corresponding in structure to Formula (IX):

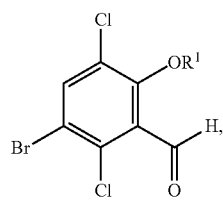
(IX)

or a salt thereof, with a debrominating agent to provide the compound or salt of Formula (X);
wherein $R^1$ is hydrogen or $C_{1-6}$-alkyl.

In another embodiment, the present disclosure relates to a process for the preparation of a compound corresponding in structure to Formula (IV-1):

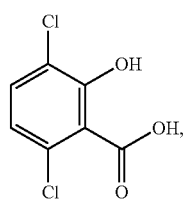

(IV-1)

or a salt thereof, the process comprising:

contacting a compound corresponding in structure to Formula (X):

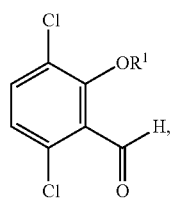

(X)

or a salt thereof, with an oxidizing agent to provide the compound or salt of Formula (VI-1);

wherein $R^1$ is hydrogen or $C_{1-6}$-alkyl.

In another embodiment, the present disclosure relates to a process for the preparation of a compound corresponding in structure to Formula (IV-1):

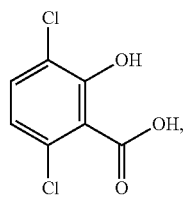

(IV-1)

or a salt thereof, the process comprising:

contacting a compound corresponding in structure to Formula (IX):

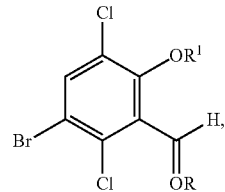

(IX)

or a salt thereof, with a debrominating agent to provide a compound corresponding in structure to Formula (X):

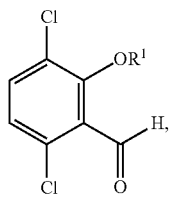

(X)

or a salt thereof; and contacting the compound or salt of Formula (X) with an oxidizing agent to provide the compound or salt of Formula (IV-1);

wherein $R^1$ is hydrogen or $C_{1-6}$-alkyl.

In another embodiment, the present disclosure relates to a process for the preparation of a compound corresponding in structure to Formula (IV-1):

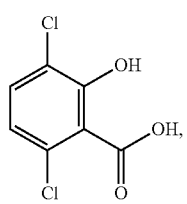

(IV-1)

or a salt thereof, the process comprising:

contacting a compound corresponding in structure to Formula (VIII):

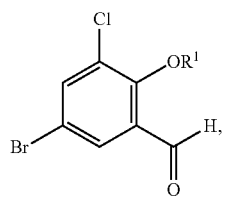

(VIII)

or a salt thereof, with a chlorinating agent to provide a compound corresponding in structure to Formula (IX):

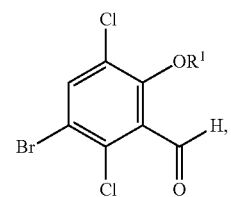

(IX)

or a salt thereof;

contacting the compound or salt of Formula (IX) with a debrominating agent to provide a compound corresponding in structure to Formula (X):

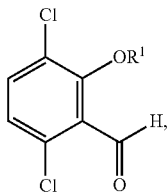
(X)

or a salt thereof; and contacting the compound or salt of Formula (X) with an oxidizing agent to provide the compound or salt of Formula (IV-1);

wherein $R^1$ is hydrogen or $C_{1-6}$-alkyl.

In another embodiment, the present disclosure relates to a process for the preparation of a compound corresponding in structure to Formula (IV-1):

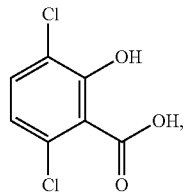
(IV-1)

or a salt thereof, the process comprising:

contacting a compound corresponding in structure to Formula (VII):

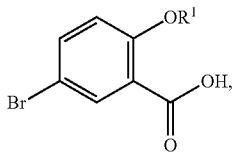
(VII)

or a salt thereof, with a first chlorinating agent to provide a compound corresponding in structure to Formula (VIII):

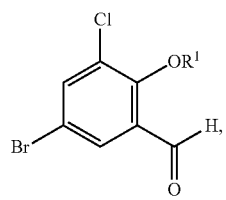
(VIII)

or a salt thereof;

contacting the compound or salt of Formula (VIII) with a second chlorinating agent to provide a compound corresponding in structure to Formula (IX):

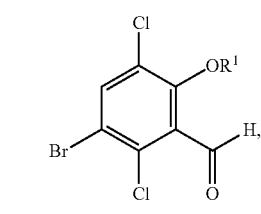
(IX)

or a salt thereof;

contacting the compound or salt of Formula (IX) with a debrominating agent to provide a compound corresponding in structure to Formula (X):

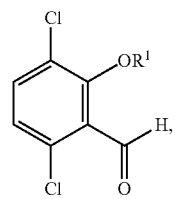
(X)

or a salt thereof; and contacting the compound or salt of Formula (X) with an oxidizing agent to provide the compound or salt of Formula (IV-1);

wherein $R^1$ is hydrogen or $C_{1-6}$-alkyl; and the first chlorinating agent and the second chlorinating agent can be the same or different.

In certain embodiments of the above-described processes relating to the compounds or salts of Formula (VII), Formula (VIII), Formula (IX), and Formula (X), $R^1$ is hydrogen, methyl, or ethyl. In one aspect, $R^1$ is hydrogen or methyl. In another aspect, $R^1$ is methyl. In another aspect, $R^1$ is hydrogen and the compounds of Formula (VII), Formula (VIII), Formula (IX), and Formula (X) correspond in structures to Formula (VII-1), Formula (VIII-1), Formula (IX-1), and Formula (X-1), respectively:

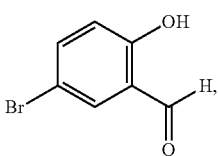
(VII-1)

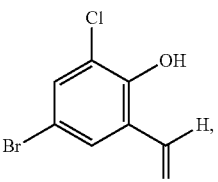
(VIII-1)

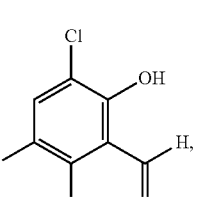
(IX-1)

and

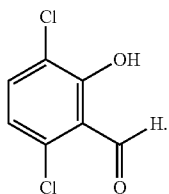

(X-1)

In general, suitable process conditions for the selective chlorination and debromination of 5-bromo-2-hydroxybenzaldehyde compounds substantially correspond to the process conditions previously described for the corresponding steps of BDCSA Process 1 and BDCSA Process 2 except as otherwise stated. A broad range of oxidizing agents and oxidation conditions can be employed to convert the compound of Formula (X) to the compound of Formula (IV-1). Examples of suitable oxidizing agents and oxidation conditions are described, for example, in Richard C. Larock, Comprehensive Organic Transformations (Wiley-VCH Vertag GmbH 1999).

VIII. CONVERSION OF 3,6-DICHLOROSALICYLIC ACID COMPOUNDS TO DICAMBA

A. Conversion of 3,6-Dichlorosalicylic Acid to Dicamba

As previously noted, the 3,6-dichlorosalicylic acid compounds prepared as described above (e.g., 3,6-dichlorosalicylic acid) can be further converted to dicamba.

Accordingly, in one embodiment, the present disclosure relates to a process for the preparation of a compound corresponding in structure to Formula (V):

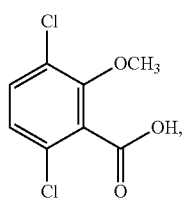

(V)

or a salt thereof, the process comprising:

contacting a compound corresponding in structure to Formula (II):

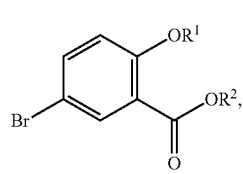

(II)

or a salt thereof, with a chlorinating agent in an acidic reaction medium to provide the compound or salt of Formula (III):

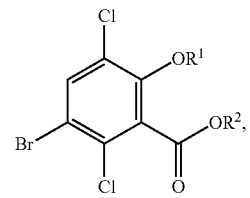

(III)

or a salt thereof;

selectively debrominating the compound or salt of Formula (III) to provide a compound corresponding in structure to Formula (IV):

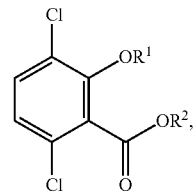

(IV)

or a salt thereof;

wherein $R^1$ is hydrogen or $C_{1-6}$-alkyl; $R^2$ is hydrogen or $C_{1-6}$-alkyl; and wherein the process further comprises converting the compound or salt of Formula (IV) to the compound or salt of Formula (V) when the compound of Formula (IV) is other than dicamba.

In certain embodiments, $R^1$ is hydrogen, methyl, or ethyl; and $R^2$ is hydrogen, methyl, or ethyl. In one aspect, $R^1$ is hydrogen or methyl; and $R^2$ is hydrogen or methyl. In another aspect, $R^1$ and $R^2$ are each hydrogen (i.e., the compound of Formula (II) is 5-bromosalicylic acid and the compound of Formula (III) is 5-bromo-3,6-dichlorosalicylic acid). In another aspect, $R^1$ and $R^2$ are each methyl. In another aspect, one of $R^1$ and $R^2$ is hydrogen and the other of $R^1$ and $R^2$ is methyl.

A number of synthetic routes for converting 3,6-dichlorosalicylic acid to dicamba have been reported in the literature and any such suitable route may be employed. For example, one approach involves methylating 3,6-dichlorosalicylic acid to provide methyl 3,6-dichloro-2-methoxybenzoate (e.g., methylation by treatment with dimethyl sulfate, dimethyl carbonate, or a halomethane such as methyl chloride, methyl bromide, or methyl iodide), and then saponifying the ester group of the methyl 3,6-dichloro-2-methoxybenzoate (e.g., saponification) to provide dicamba as shown in Scheme 6 below:

Scheme 6

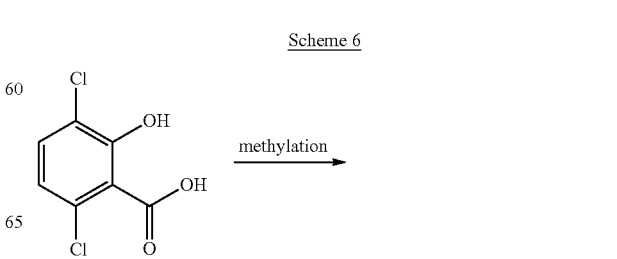

-continued

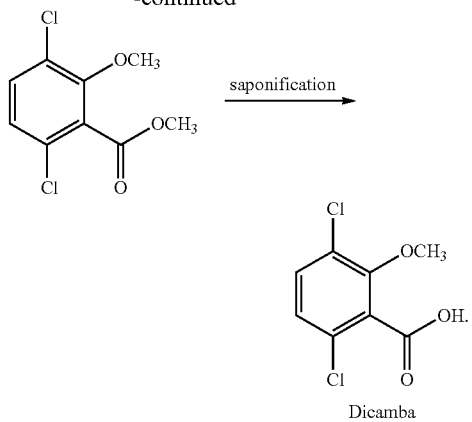

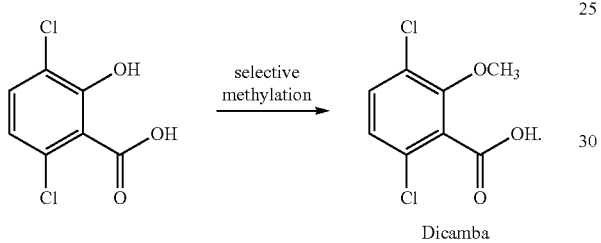

Another approach involves selectively methylating 3,6-dichlorosalicylic acid to provide dicamba as shown in Scheme 7 below:

Scheme 7

Among the various publications that report synthetic methods employing 3,6-dichlorosalicylic acid as a starting material or an intermediate in the preparation of dicamba are, for example, the following:

(a) U.S. Pat. No. 3,345,157 reports a process for methylating 3,6-dichlorosalicylic acid to provide dicamba.

(b) U.S. Pat. No. 4,161,611 reports a process for methylating 3,6-dichlorosalicylic acid to provide dicamba.

(c) Matyakh, et al., "2-Methoxy-3,6-dichloro-benzoic acid," Otkrytiya, Izobret. Prom. Obraztsy, Tovarnye, Znake 1973, 50 (18), 177-178, reports a process for methylating a 3,6-dichlorosalicylic acid sodium salt to provide dicamba.

(d) Zhang, et al., "Study on the 0-Alkylation for 3,6-dichlorosalicylic Acid by Chloromethane," Huangong Shikan 2002, 16 (12) 45-48 (Ch.), reports the O-alkylation of 3,6-dichlorosalicylic acid to provide dicamba.

(e) CN102942474A and CN 102838483A report a process for methylating 3,6-dichlorosalicylic acid with chloromethane to provide dicamba.

(f) CN102125035B reports a process for methylating 3,6-dichlorosalicylic acid with dimethyl carbonate to provide dicamba.

(g) Chinese patent application CN1830942A report a process for methylating 3,6-dichlorosalicylic acid with dimethyl sulfate to provide dicamba.

(h) U.S. Pat. No. 3,013,054 reports a process for preparing dicamba that proceeds through a 2,5-dichlorophenol intermediate.

(i) Zhang, et al., "Synthesis of Herbicide Dicamba," Nongyao 2002, 41 (11), 13-14 (Ch.), reports a process for preparing dicamba that proceeds through a 2,5-dichlorophenol intermediate.

(j) Zhang, et al., "Study on the Preparation of Dicamba," Nongyao 2002, 41 (7), 15-17 (Ch.), reports a process for preparing dicamba that proceeds through a 2,5-dichlorophenol intermediate.

(k) Eckstein, et al., Przem. Chem. 1979, 58 (10), 533-536 (Pol.), reports a process for preparing dicamba that proceeds through a 2,5-dichlorophenol intermediate.

In one embodiment, the present disclosure relates to a process for the preparation of a compound corresponding in structure to Formula (V):

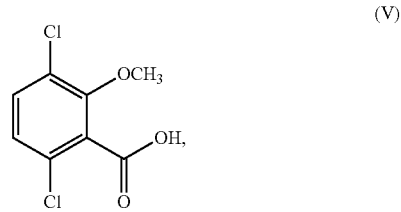 [SMILES: COc1c(Cl)ccc(Cl)c1C(=O)O]

or a salt thereof, the process comprising:
contacting a compound corresponding in structure to Formula (II-1):

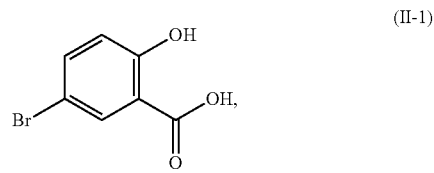 [SMILES: O=C(O)c1cc(Br)ccc1O]

or a salt thereof, with a chlorinating agent in an acidic reaction medium to provide a compound corresponding in structure to Formula (III-1):

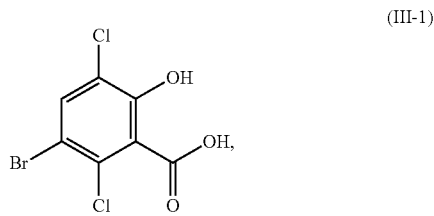 [SMILES: O=C(O)c1c(O)c(Cl)cc(Br)c1Cl]

or a salt thereof;
selectively debrominating the compound or salt of Formula (III-1) to provide a compound corresponding in structure to Formula (IV-1):

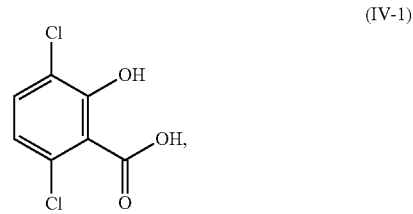 [SMILES: O=C(O)c1c(Cl)ccc(Cl)c1O]

or a salt thereof;
methylating the compound or salt of Formula (IV-1) to provide a compound corresponding in structure to Formula (IV-2):

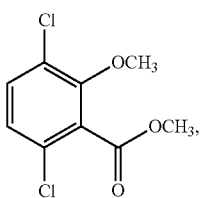

(IV-2)

or a salt thereof; and saponifying the compound or salt of Formula (IV-2) to provide the compound or salt of Formula (V).

In another embodiment, the present disclosure relates to a process for the preparation of a compound corresponding in structure to Formula (V):

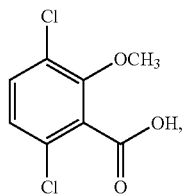

(V)

or a salt thereof, the process comprising:

contacting a compound corresponding in structure to Formula (II-1):

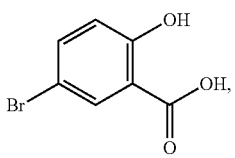

(II-1)

or a salt thereof, with a chlorinating agent in an acidic reaction medium to provide a compound corresponding in structure to Formula (III-1):

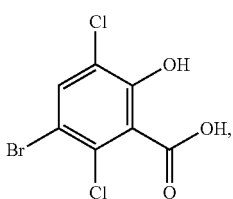

(III-1)

or a salt thereof;

selectively debrominating the compound or salt of Formula (III-1) to provide a compound corresponding in structure to Formula (IV-1):

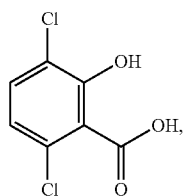

(IV-1)

or a salt thereof; and selectively methylating the compound or salt of Formula (IV-1) to provide the compound or salt of Formula (V).

In another embodiment, the present disclosure relates to a process for the preparation of a compound corresponding in structure to Formula (V):

(V)

or a salt thereof, the process comprising:

contacting a compound corresponding in structure to Formula (I-1):

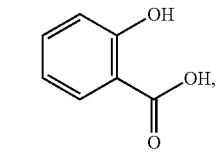

(I-1)

or a salt thereof, with a brominating agent in an acidic reaction medium comprising sulfuric acid to provide a compound corresponding in structure to Formula (II-1):

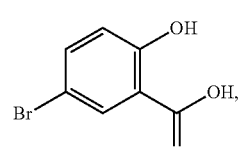

(II-1)

or a salt thereof;

contacting the compound or salt of Formula (II-1) with a first chlorinating agent without first isolating the compound or salt of Formula (II-1) from the reaction medium to provide a compound corresponding in structure to Formula (VI-1):

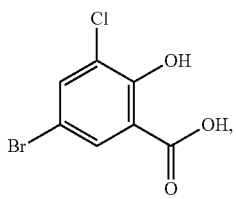
(VI-1)

or a salt thereof; and contacting the compound or salt of Formula (VI-1) with a second chlorinating agent to provide the compound or salt of Formula (III-1):

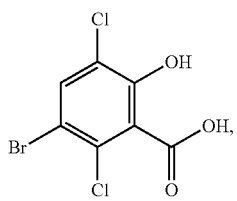
(III-1)

or a salt thereof; wherein the first chlorinating agent and the second chlorinating agent can be the same or different;

selectively debrominating the compound or salt of Formula (III-1) to provide a compound corresponding in structure to Formula (IV-1):

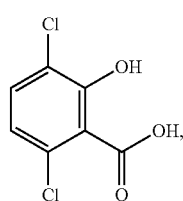
(IV-1)

or a salt thereof;

methylating the compound or salt of Formula (IV-1) to provide a compound corresponding in structure to Formula (IV-2):

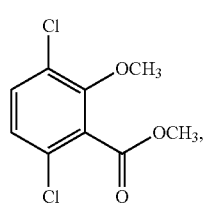
(IV-2)

or a salt thereof; and saponifying the compound or salt of Formula (IV-2) to provide the compound or salt of Formula (V).

In one embodiment, the present disclosure relates to a process for the preparation of a compound corresponding in structure to Formula (V):

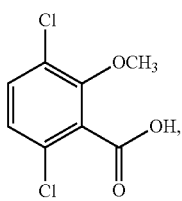
(V)

or a salt thereof, the process comprising:

contacting a compound corresponding in structure to Formula (I):

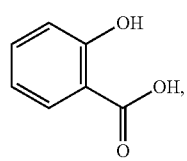
(I-1)

or a salt thereof, with a brominating agent in an acidic reaction medium comprising sulfuric acid to provide a compound corresponding in structure to Formula (II-1):

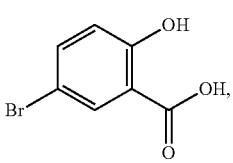
(II-1)

or a salt thereof;

contacting the compound or salt of Formula (II-1) with a first chlorinating agent without first isolating the compound or salt of Formula (II-1) from the reaction medium to provide a compound corresponding in structure to Formula (VI-1):

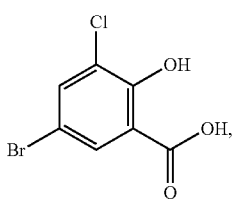
(VI-1)

or a salt thereof; and contacting the compound or salt of Formula (VI) with a second chlorinating agent to provide the compound or salt of Formula (III-1):

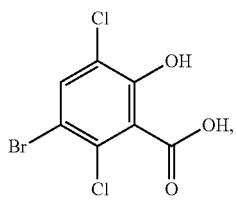

(III-1)

or a salt thereof; wherein the first chlorinating agent and the second chlorinating agent can be the same or different;

selectively debrominating the compound or salt of Formula (III-1) to provide a compound corresponding in structure to Formula (IV-1):

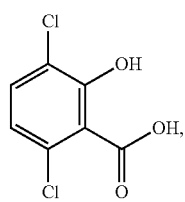

(IV-1)

or a salt thereof; and selectively methylating the compound or salt of Formula (IV-1) to provide the compound or salt of Formula (V).

In another embodiment, the present disclosure relates to a process for the preparation of a compound corresponding in structure to Formula (V):

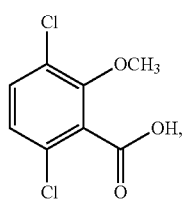

(V)

or a salt thereof, the process comprising:

contacting a compound corresponding in structure to Formula (VII-1):

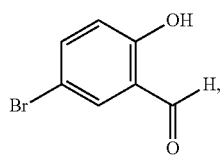

(VII-1)

or a salt thereof, with a first chlorinating agent to provide a compound corresponding in structure to Formula (VIII-1):

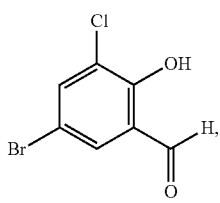

(VIII-1)

or a salt thereof;

contacting the compound or salt of Formula (VIII-1) with a second chlorinating agent to provide a compound corresponding in structure to Formula (IX-1):

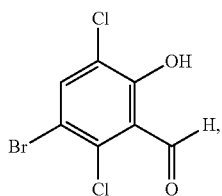

(IX-1)

or a salt thereof; wherein the first chlorinating agent and the second chlorinating agent can be the same or different;

contacting the compound or salt of Formula (IX-1) with a debrominating agent to provide a compound corresponding in structure to Formula (X-1):

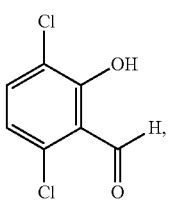

(X-1)

or a salt thereof; and contacting the compound or salt of Formula (X-1) with an oxidizing agent to provide a compound corresponding in structure to Formula (IV-1):

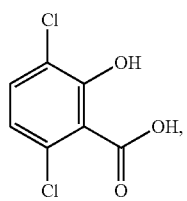

(IV-1)

or a salt thereof;

methylating the compound or salt of Formula (IV-1) to provide a compound corresponding in structure to Formula (IV-2):

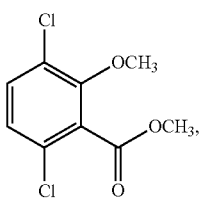

(IV-2)

or a salt thereof; and saponifying the compound or salt of Formula (IV-2) to provide the compound or salt of Formula (V).

In another embodiment, the present disclosure relates to a process for the preparation of a compound corresponding in structure to Formula (V):

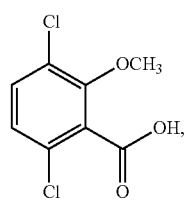

(V)

or a salt thereof, the process comprising:

contacting a compound corresponding in structure to Formula (VII-1):

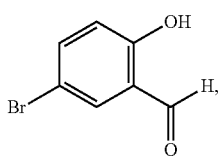

(VII-1)

or a salt thereof, with a first chlorinating agent to provide a compound corresponding in structure to Formula (VIII-1):

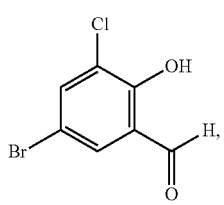

(VIII-1)

or a salt thereof;

contacting the compound or salt of Formula (VIII-1) with a second chlorinating agent to provide a compound corresponding in structure to Formula (IX-1):

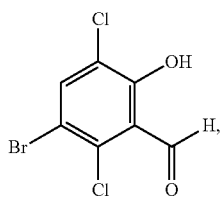

(IX-1)

or a salt thereof; wherein the first chlorinating agent and the second chlorinating agent can be the same or different;

contacting the compound or salt of Formula (IX-1) with a debrominating agent to provide a compound corresponding in structure to Formula (X-1):

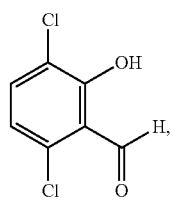

(X-1)

or a salt thereof; and contacting the compound or salt of Formula (X-1) with an oxidizing agent to provide a compound corresponding in structure to Formula (IV-1):

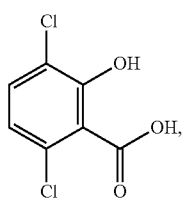

(IV-1)

or a salt thereof; and selectively methylating the compound or salt of Formula (IV-1) to provide the compound or salt of Formula (V).

In alternative embodiments of the process described immediately above, the process employs the Compounds of Formula (VII), Formula (VIII), Formula (IX), and Formula (X) in place of the Compounds of Formula (VII-1), Formula (VIII-1), Formula (IX-1), and Formula (X-1) to provide a Compound of Formula (IV) wherein $R^2$ is hydrogen. When $R^1$ is other than methyl, converting the Compound or salt of Formula (IV) is further needed to provide the Compound or salt of Formula (V).

B. Conversion of 5-Bromo-3,6-Dichlorosalicylic Acid to Dicamba

Alternatively, the 5-bromo-3,6-dichlorosalicylic acid compounds prepared as described above (e.g., 5-bromo-3,6-dichlorosalicylic acid) can be first converted to the corresponding methyl ester compounds. Dicamba is converted by selective debromination of the methyl ester compounds (e.g., methyl 3-bromo-2,5-dichloro-6-methoxybenzoate) followed by saponification.

Accordingly, in one embodiment, the present disclosure relates to a process for the preparation of a compound corresponding in structure to Formula (V):

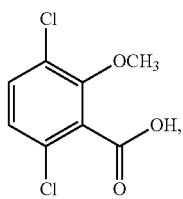

or a salt thereof, the process comprising:

contacting a compound corresponding in structure to Formula (III-1):

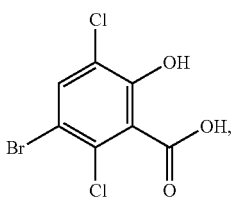

or a salt thereof, with a methylating agent to provide a compound corresponding in structure to Formula (III-2):

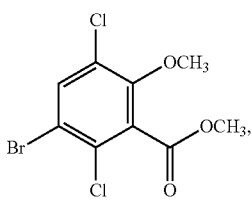

or a salt thereof;

selectively debrominating the compound or salt of Formula (III-2) to provide a compound corresponding in structure to Formula (IV-2):

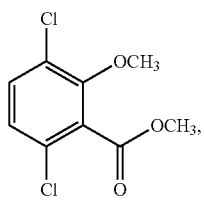

or a salt thereof; and saponifying the compound or salt of Formula (IV-2) to provide the compound or salt of Formula (V).

Accordingly, the approach involves methylation of the 5-bromo-3,6-dichlorosalicylic acid compounds, selective debromination, and saponification to provide dicamba as shown in Scheme 8 below:

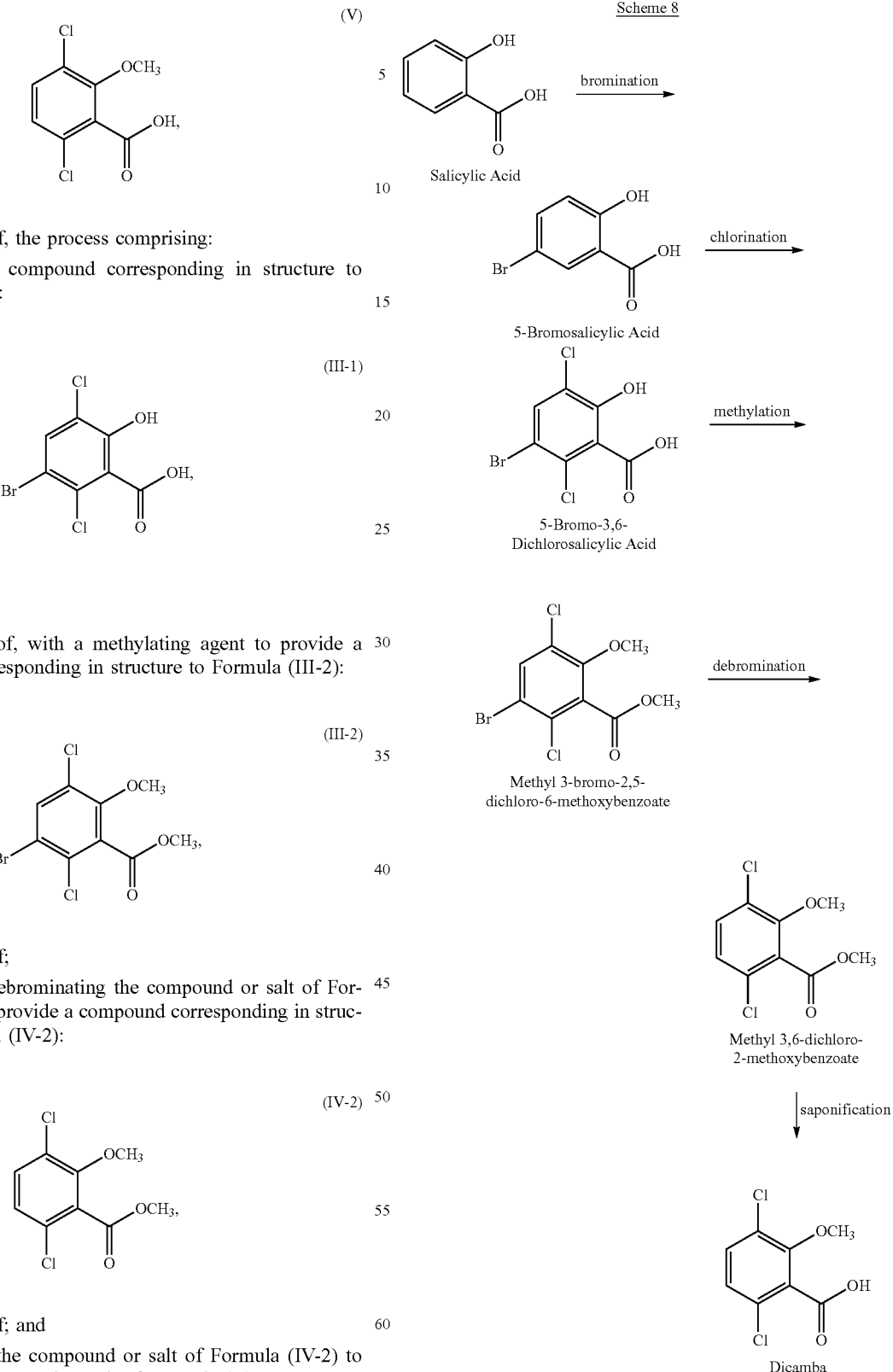

In one embodiment, the present disclosure relates to a process for the preparation of a compound corresponding in structure to Formula (V):

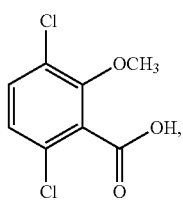
(V)

or a salt thereof, the process comprising:

contacting a compound corresponding in structure to Formula (II-1):

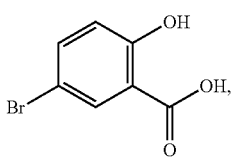
(II-1)

or a salt thereof, with a chlorinating agent in an acidic reaction medium to provide a compound corresponding in structure to Formula (III-1):

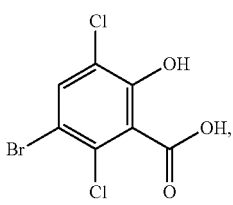
(III-1)

or a salt thereof;

methylating the compound or salt of Formula (III-1) to provide a compound corresponding in structure to Formula (III-2):

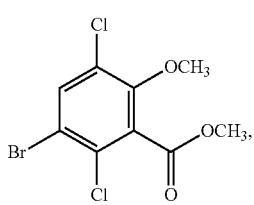
(III-2)

or a salt thereof;

selectively debrominating the compound or salt of Formula (III-2) to provide a compound corresponding in structure to Formula (IV-2):

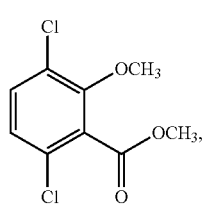
(IV-2)

or a salt thereof; and saponifying the compound or salt of Formula (IV-2) to provide the compound or salt of Formula (V).

In another embodiment, the present disclosure relates to a process for the preparation of a compound corresponding in structure to Formula (V):

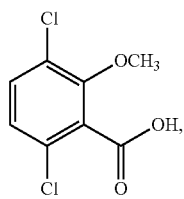
(V)

or a salt thereof, the process comprising:

contacting a compound corresponding in structure to Formula (I-1):

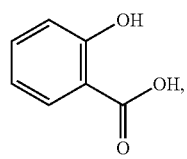
(I-1)

or a salt thereof, with a brominating agent in an acidic reaction medium comprising sulfuric acid to provide a compound corresponding in structure to Formula (II-1):

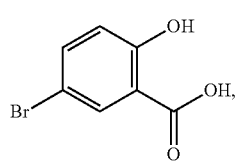
(II-1)

or a salt thereof;

contacting the compound or salt of Formula (II-1) with a first chlorinating agent without first isolating the compound or salt of Formula (II-1) from the reaction medium to provide a compound corresponding in structure to Formula (V1-1):

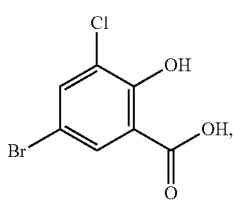

(VI-1)

or a salt thereof; and
contacting the compound or salt of Formula (VI-1) with a second chlorinating agent to provide the compound or salt of Formula (III-1):

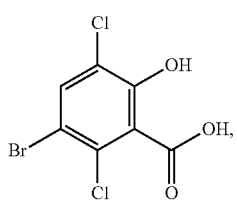

(III-1)

or a salt thereof; wherein the first chlorinating agent and the second chlorinating agent can be the same or different;

methylating the compound or salt of Formula (III-1) to provide a compound corresponding in structure to Formula (III-2):

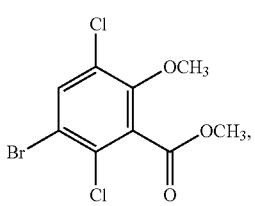

(III-2)

or a salt thereof;

selectively debrominating the compound or salt of Formula (III-2) to provide a compound corresponding in structure to Formula (IV-2):

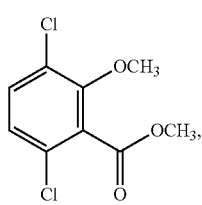

(IV-2)

or a salt thereof; and
saponifying the compound or salt of Formula (IV-2) to provide the compound or salt of Formula (V).

In each of the embodiments disclosed in the present application where desirable and appropriate, the process may further comprise isolation and/or purification of one or more of the intermediates employed in the process before reacting the intermediate(s) in a subsequent step of the process. For example, the disclosed processes may further comprise one or more of the following steps where desirable and appropriate: (1) isolating and/or purifying the compound or salt of Formula (II), (2) isolating and/or purifying the compound or salt of Formula (III), (3) isolating and/or purifying the compound or salt of Formula (IV), and/or (4) isolating or purifying the compound or salt of Formula (V) (i.e., dicamba).

IX. COMPOUNDS

In additional embodiments, the present disclosure relates to novel compounds of the processes as described above.

In one embodiment, the present disclosure relates to a compound corresponding in structure to Formula (III):

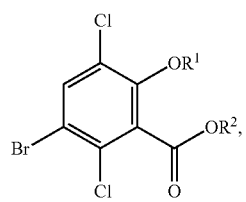

(III)

or a salt thereof, wherein $R^1$ is hydrogen or $C_{1-6}$-alkyl; and $R^2$ is hydrogen or $C_{1-6}$-aylkyl. In one aspect, $R^1$ is hydrogen, methyl, or ethyl; and $R^2$ is hydrogen, methyl, or ethyl. In another aspect, $R^1$ is hydrogen or methyl; and $R^2$ is hydrogen or methyl. In another aspect, $R^1$ and $R^2$ are each hydrogen. In another aspect, $R^1$ and $R^2$ are each methyl.

In one embodiment, the present disclosure relates to a compound corresponding in structure to Formula (III-1):

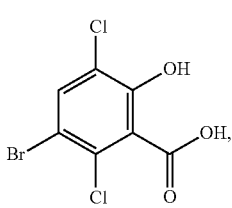

(III-1)

or a salt thereof.

In one embodiment, the present disclosure relates to a compound corresponding in structure to Formula (III-2):

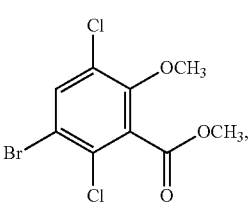

(III-2)

or a salt thereof.

As previously discussed, such compounds or salts of Formula (III); Formula (III-1); and Formula (III-2) are useful, for example, as intermediates in processes for the preparation of dicamba.

In one embodiment, the present disclosure relates to a compound corresponding in structure to Formula (IX):

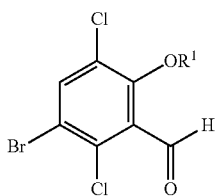

(IX)

or a salt thereof, wherein $R^1$ is hydrogen or $C_{1-6}$-alkyl. In one aspect, $R^1$ is hydrogen, methyl, or ethyl. In another aspect, $R^1$ is hydrogen or methyl. In another aspect, $R^1$ is hydrogen.

In one embodiment, the present disclosure relates to a compound corresponding in structure to Formula (IX-1):

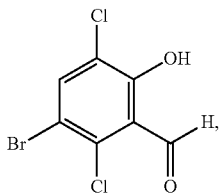

(IX-1)

or a salt thereof.

As previously discussed, such compounds or salts of Formula (IX) and Formula (IX-1) are useful, for example, as intermediates in processes for the preparation of dicamba.

X. EXAMPLES

The following non-limiting examples are provided to further illustrate the present invention.

Example 1: Analytical Methods

A. Reverse-Phase High-Performance Liquid Chromatography ("RP-HPLC") Method

RP-HPLC analysis used to monitor reactions was conducted on an Agilent 1260 Infinity Analytical-Scale LC/MS Purification System equipped with a diode array UV detector and monitored at 315 nm. The column was an Agilent Poroshell 120 C-18EC, 4.6×50 mm, 2.7 micron with a pre-column filter. The RP-HPLC was conducted at a flow rate of 2 mL/minute of mobile phase water (0.05% trifluoroacetic acid) and acetonitrile as described in Table 1-A below:

TABLE 1-A

| RP-HPLC Method | | |
|---|---|---|
| TIME | % WATER | % ACETONITRILE |
| 0.00 | 70 | 30 |
| 0.25 | 70 | 30 |

TABLE 1-A-continued

| RP-HPLC Method | | |
|---|---|---|
| TIME | % WATER | % ACETONITRILE |
| 4.00 | 5 | 95 |
| 4.25 | 70 | 30 |
| 5.00 | 70 | 30 |

B. Nuclear Magnetic Resonance Method

Nuclear magnetic resonance analysis was run on a Bruker 600 MHz instrument. Deuterated solvents from Cambridge Isotope Laboratories, Ltd., including methanol-$d_4$, chloroform-d, and dimethylsulfoxide-$d_6$, were used as required.

Example 2: Preparation of 5-Bromosalicylic Acid

Salicylic acid (6.0 g, 43.47 mmol) and concentrated sulfuric acid (98%, 21.5 mL) were charged into a 250 mL three-necked flask equipped with a temperature probe, heating mantle, overhead stirrer, and an inlet for a Teflon needle/syringe pump to deliver bromine. Stirring was commenced to dissolve the salicylic acid, which was slightly exothermic. Once the mixture reached ambient temperature, the syringe was loaded with a slight excess of bromine to ensure delivery of 0.575 equivalents over 5 minutes. As bromine was added to the rapidly stirred solution, a slight exotherm was observed. Once the addition was complete, the reaction mixture was stirred for an additional five minutes before heating to 60° C., which required about 15 minutes. The reaction mixture was stirred at 60° C. for a total of 60 minutes, then allowed to cool to ambient temperature. Ice water (about 100 g) was slowly added to the reaction mixture, which caused a white solid to form. During the ice water addition, the temperature rose to about 50° C. to 60° C. The reaction mixture was cooled in an ice bath to 10° C., then filtered through a sintered glass funnel. The precipitate was washed with 4×30 mL of cold water, resuspending the cake each time before extracting the water wash. The cake was air dried for 30 minutes, then dried in vacuo (55° C.) overnight to afford the title compound as a white solid (8.7 g, 92%). RP-HPLC (315 nm) and $^1$H NMR (600 MHz, DMSO-$d_6$) indicated the crude material had the following composition: 5-bromosalicylic acid (96%), 3-bromosalicylic acid (0.4%) and 3,5-dibromosalicylic acid (3.5%).

Analytical data for 5-bromosalicylic acid: $^1$H NMR (600 MHz, DMSO-$d_6$) δ 11.9-10.9, 7.85, 7.65, 6.95. LCMS (ESI) m/z 214.9 (M−H).

Example 3: Preparation of 5-Bromosalicylic Acid (Alternative Conditions)

Salicylic acid was brominated with molecular bromine as described in Example 2 except that the reagent equivalents and heating time and temperature upon completion of bromine addition were varied as indicated in Table 3-A below. Table 3-A also reports the salicylic acid ("SA"), 3-bromosalicylic acid ("3-Br-SA"), 5-bromosalicylic acid ("5-Br-SA), and 3,5-dibromosalicylic acid ("3,5-$Br_2$-SA") present in the resulting crude material as determined by RP-HPLC peak areas (which were adjusted using response factors of the respective analytes below).

TABLE 3-A

| No. | Conditions | Br₂ (Equiv.) | Time (Min.) | Temp (° C.) | SA (%) | 3-Br-SA (%) | 5-Br-SA (%) | 3,5-Br₂-SA (%) |
|---|---|---|---|---|---|---|---|---|
| 1 | A | 1.0 | 40 | 30 to 100 | 0.0 | 1.6 | 80.2 | 18.2 |
| 2 | A | 1.0 | 30 | 30 to 60 | 0.2 | 5.9 | 88.1 | 5.8 |
| 3 | A | 1.0 | 120 | 30 | 5.8 | 6.2 | 87.6 | 0.4 |
| 4 | A | 1.0 | (12 h) | <20 | 6.9 | 8.7 | 83.6 | 0.5 |
| 5 | B | 1.0 | 120 | 20 | 22.5 | 2.0 | 74.3 | 1.1 |
| 6 | B | 1.75 | 120 | 20 | 0.0 | 1.0 | 95.5 | 3.5 |
| 7 | C | 1.0 | 60 | 20 | 0.0 | 0.0 | 90.9 | 9.1 |
| 8 | C | 0.90 | 60 | 20 | 0.0 | 0.9 | 95.5 | 3.6 |
| 9 | C | 0.80 | 60 | 20 | 0.0 | 0.8 | 95.7 | 3.5 |
| 10 | C | 0.70 | 60 | 20 | 0.0 | 1.1 | 95.5 | 3.4 |
| 11 | C | 0.60 | 60 | 20 | 0.0 | 0.4 | 94.5 | 5.0 |
| 12 | C | 0.56 | 60 | 20 | 0.9 | 2.2 | 94.9 | 2.0 |
| 13 | C | 0.50 | 60 | 20 | 14.5 | 2.3 | 82.7 | 0.6 |

Conditions A, B, and C referenced in Table 3-A are more fully described in Table:1-R below

TABLE 3-B

| | EQUIVALENTS | | |
|---|---|---|---|
| REAGENTS | CONDITION A | CONDITION B | CONDITION C |
| Salicylic Acid | 1.0 | 1.0 | 1.0 |
| H₂SO₄ | 2.0 (Added as 98% H₂SO₄) | To 1.0M (Added as 98% H₂SO₄) | To 1.0M (Added as 98% H₂SO₄) |
| Br₂ | 1.0 (Added as 2.0M Br₂ solution in acetic acid) | 1.0 (Added as 10.0M Br₂ solution in acetic acid) | 1.0 (Br₂ neat) |
| Acetic Acid | To 1.0M | | |

Example 4: Preparation of 5-Bromo-3,6-dichlorosalicylic Acid Using Sodium Hypochlorite 5-Bromosalicylic acid (1.0 g, 4.6 mmol) was dissolved in 2.5 M sodium hydroxide (3.7 mL). The resulting solution was cooled in an ice bath to 0° C. at which time a 12% by weight solution of sodium hypochlorite (4.6 mL) was added drop-wise. Once the addition was completed, concentrated HCl was added drop-wise until the mixture became turbid. The reaction was warmed to 40° C. for 5 hours. An aliquot of the reaction mixture was removed and analyzed by RP-HPLC which indicated that the major product was 5-bromo-3-chlorosalicylic acid when compared with a known standard. Overnight heating at 40° C. with an additional 4.6 mL of 12% by weight solution of sodium hypochlorite (4.6 mL) did not produce the desired 5-bromo-3,6-dichlorosalicylic acid.

Example 5: Preparation of 5-Bromo-3,6-dichlorosalicylic Acid Using Trichloroisocyanuric Acid in Concentrated Sulfuric Acid 5-Bromosalicylic acid (1.0 g, 4.6 mmol) was dissolved in concentrated sulfuric acid (98%, 10 mL), which caused a mild exotherm. Iodine (25 mg, 0.1 mmol) was added, and the resulting reaction mixture was cooled to 0° C. Trichloroisocyanuric acid (0.440 g, 1.90 mmol) was added, and the reaction mixture was stirred at 0° C. for one hour. An aliquot of the reaction mixture was removed and analyzed by RP-HPLC, which indicated that the major product was 5-bromo-3-chlorosalicylic acid when compared with a known standard. Additional trichloroisocyanuric acid (0.440 g, 1.90 mmol) was added, and the reaction mixture was warmed to ambient temperature for one hour, followed by warming to 40° C. for one hour, and finally to 70° C. for two hours. An aliquot of the reaction mixture was removed and analyzed by RP-HPLC. 5-Bromo-3-chlorosalicylic acid was still present, along with two more polar components and a less polar component. The reaction mixture was poured into crushed ice and extracted with ethyl acetate. The organic layer was washed with brine, dried over anhydrous magnesium sulfate, filtered and concentrated in vacuo to a yellow solid. ¹H NMR (600 MHz, DMSO-d₆) showed a mixture of four compounds: 5-bromo-3-chlorosalicylic acid, 5-bromo-3,6-dichlorosalicylic acid, 3,5,6-trichlorosalicylic acid, and a compound of unknown structure in a 20:35:20:25 ratio.

Example 6: Preparation of 5-Bromo-3,6-dichlorosalicylic Acid Using Trichloroisocyanuric Acid in Oleum (Fuming Sulfuric Acid)

Iodine (29 mg, 0.115 mmol) was suspended in 20% oleum (50 mL) and the resulting mixture was stirred at ambient temperature for five minutes at which time 5-bromosalicylic acid (5.00 g, 23.04 mmol) was added. The resulting suspension was cooled with an ice-bath until an internal temperature of 5° C. was reached. Trichloroisocyanuric acid (7.74 mmol) was added as a solid in one portion. The cooling bath was removed and the reaction mixture was allowed to self-heat over a 75 minute period to a temperature of 30° C. The reaction mixture was again placed in a cooling bath about two hours after the initial removal of the cooling bath and iodine (88 mg, 0.346 mmol) was added along with trichloroisocyanuric acid (7.74 mmol). The resulting mixture was allowed to stir overnight. The reaction mixture was cooled to 5° C. with an ice bath and then slowly poured onto crushed ice. The aqueous reaction mixture was extracted into ethyl acetate (2×100 mL). The combined organic layers were filtered through a pad of Celite to remove the insoluble material. The resulting filtrate was washed with brine, NaHSO$_3$ solution (10 mL), dried (MgSO$_4$), filtered, and concentrated. A portion of the resulting solid (2.0 g) was subjected to reverse phase chromatography (Water with 0.1% TFA: Acetonitrile) to give the desired product (0.730 g) as a tan crystalline solid. $^1$H-NMR (600 MHz, DMSO-d$_6$) δ 12.8-10.0 (br s, 2H), 7.91 (s, 1H); ESI-MS m/z 284.9 (M+H).

Example 7: Preparation of 5-Bromo-3,6-dichlorosalicylic Acid Using Trichloroisocyanuric Acid in Oleum (Alternative Conditions)

5-Bromosalicylic acid was di-chlorinated using trichloroisocyanuric acid (ACL® 90, Occidental Chemical Corporation) and catalytic iodine in fuming sulfuric acid as described in Example 6 except that the reaction conditions were varied as indicated in Table 7-A below. Table 7-A also reports the yield of 5-bromo-3,6-dichlorosalicylic acid under the different conditions.

TABLE 7-A

| No. | Reaction Temp. | I$_2$ (Mole %) | BSA* Scale (mmol) | TCICA* (mmol) | Active Chlorine (Equivalents) | Reaction Time (Hours) | BDCSA* % Yield |
|---|---|---|---|---|---|---|---|
| 1 | 5° C. to ambient | 2.25 | 23.0 | 17.6 | 2.3 | 20 | 78**, 77*** |
| 2 | 5° C. to 30° C. | 1.5 | 46.0 | 36.8 | 2.4 | 5 | 88*** |
| 3 | 5° C. to 40° C. | 2.1 | 4.6 | 3.5 | 2.3 | 4 | 73** |
| 4 | 5° C. to 40° C. | 2.5 | 4.6 | 3.1 | 2.05 | 4 | 66** |
| 5 | 5° C. to 40° C. | 1 | 4.6 | 3.1 | 2.0 | 4 | 76**, 79*** |
| 6 | 5° C. to 40° C. | 1 | 4.6 | 3.1 | 2.05 | 4 | 73*** |
| 7 | 5° C. to 40° C. | 1 | 23.0 | 15.3 | 2.0 | 3 | 61*** |
| 8 | 5° C. to 30° C. | 0.5 | 23.0 | 16.0 | 2.09 | 3.5 | 67*** |
| 9 | 5° C. to 40° C. | 0.5 | 23.0 | 15.5 | 2.02 | 4 | 80*** |
| 10 | 5° C. to 40° C. | 0.5 | 46.0 | 31.9 | 2.08 | 4 | 79*** |
| 11 | 5° C. to 35° C. | 0.5 | 55.3 | 37.2 | 2.02 | 5 | 82*** |
| 12 | 5° C. to 35° C. | 0.5 | 69.0 | 50.6 | 2.2 | 6 | 85*** |

*BSA: 5-bromosalicylic acid; BDCSA: 5-bromo-3,6-dichlorosalicylic acid; TCICA: trichloroisocyanuric acid
**Yields based on RP-HPLC peak integrations at 315 nm.
***Yields based on integrations of aromatic signals in the $^1$H-NMR (600 MHz, DMSO-d$_6$) spectrum of the crude isolated product.

Example 8: Preparation of 5-Bromo-3,6-dichlorosalicylic Acid Using Chlorine Gas Iodine (30 mg, 0.118 mmol) and 5-bromosalicylic acid (12.0 g, 55.3 mmol) were suspended in oleum (120 mL), and the resulting suspension was cooled with an ice-bath until an internal temperature of 10° C. was reached. The bath was removed, and chlorine gas was bubbled into the reaction mixture for 10 hours. After two hours, an additional 30 mg (0.118 mmol) of iodine was added. After 3.5 hours at ambient temperature, the mixture became homogeneous. After 10 hours of bubbling chlorine into the mixture at ambient temperature, the mixture was a suspension. Stirring was stopped and the precipitate was allowed to settle. The oleum was decanted from the precipitate. The precipitate was washed with ice-water and dried in vacuo to afford 9.9 g of an off-white solid. The oleum was poured into crushed ice (about 700 g), and extracted with ethyl acetate. The organic layer was washed with brine, dried over anhydrous magnesium sulfate, filtered, and concentrated in vacuo to afford 4.7 g of an off-white solid. This solid was combined with the solid precipitate from above to afford 14.6 g (92%) of the title compound as an off-white solid. RP-HPLC and $^1$H NMR on the solid indicated a purity level of about 85%. $^1$H-NMR (600 MHz, DMSO-d$_6$) δ 12.8-10.0 (br s, 2H), 7.91 (s, 1H); ESI-MS m/z 284.9 (M+H).

Example 9: Preparation of 3,6-dichlorosalicylic Acid

A mixture containing 5-bromo-3,6-dichlorosalicylic acid (5.0 g, 18 mmol), sodium acetate (1.50 g, 18.5 mmol), and 10% Pd/C (50% water content, 250 mg) in glacial acetic acid (80 mL) was hydrogenated (1 atmosphere) at ambient temperature for 16 hours. The catalyst was filtered through Celite and washed with acetic acid. The solution was concentrated in vacuo. The remaining solid was partitioned between 1.0 M HCl solution and ethyl acetate. The organic layer was washed with brine, dried over magnesium sulfate, filtered, and concentrated in vacuo to afford 3.5 g (97%) of a white solid. RP-HPLC and $^1$H NMR (600 MHz, DMSO-d$_6$) of the crude material indicated a purity of about 90%, the remaining material being unreacted starting material (about 3%) and 3-chlorosalicylic acid (7%). Analytical data for 3,6-dichlorosalicylic acid: $^1$H NMR (600 MHz, DMSO-d$_6$) 14.5-13.5, 7.34, 6.77; LCMS (ESI) m/z 204.7 (M−H).

Example 10: Preparation Of 3,6-dichlorosalicylic Acid (Alternative Conditions)

5-Bromo-3,6-dichlorosalicylic was hydro-debrominated to provide 3,6-dichlorosalicylic acid as described in Example 9 except that the reaction conditions were varied as indicated in Table 10-A below. Table 10-A also reports the yield of 3,6-dichlorosalicylic acid under the different conditions.

TABLE 10-A

| No. | Catalyst | Solvent | Base | $H_2$ Pressure/ $H_2$ source | Temp. | % Yield DCSA |
|---|---|---|---|---|---|---|
| 1 | Pd/C | Methanol | — | $NH_4CO_2H$ | Reflux | 10 |
| 2 | Pd/C | Methanol | Sodium Hydroxide | $NH_4CO_2H$ | Reflux | 11 |
| 3 | Pd(OH)$_2$/C | Ethanol | — | $NH_4CO_2H$ | 80° C. | 5 |
| 4 | Pd/C | Acetic Acid | Potassium Acetate | 1 atm | Ambient | 75 |
| 5 | Pd/C | Acetic Acid | Sodium Acetate | 1 atm | Ambient | 85 |
| 6 | Pd/C | Methanol/Water | Sodium Hydroxide | 1 atm | Ambient | 5 |
| 7 | Pd/C | Methanol/Water | Potassium bicarbonate | 1 atm | Ambient | 40 |
| 8 | Pd(OH)$_2$/C | Acetic Acid | Potassium Acetate | 1 atm | Ambient | <1 |
| 9 | Pd/BaSO$_4$ | Acetic Acid | Potassium Acetate | 1 atm | Ambient | <1 |
| 10 | Pd/C | Ethyl Acetate | Potassium Acetate | 1 atm | Ambient | 90 |
| 11 | Pd/C | Butanoic Acid | Potassium Acetate | 1 atm | Ambient | 90 |
| 12 | Pd/C | Hexanoic Acid | Potassium Acetate | 1 atm | Ambient | 65 |
| 13 | Pd/C | Acetic Acid | — | 1 atm | Ambient | 5 |
| 14 | Pd/C | Acetic Acid | Potassium Acetate (cat.) | 1 atm | Ambient | 15 |
| 15 | Pd/C | Acetic Acid | Potassium Acetate (3 eq.) | 1 atm | Ambient | 45 |
| 16 | Raney Nickel | Ethyl Acetate | Potassium Acetate | 1 atm | Ambient | <1 |
| 17 | Pd/C | Acetic Acid | Sodium Hydroxide | 1 atm | Ambient | 85 |
| 18 | Pd/C | Acetic Acid/Ethyl Acetate | Sodium Acetate | 1 atm | Ambient | 95% |
| 19 | Pd/C | Ethyl Acetate/Water | Sodium Hydroxide | 1 atm | Ambient | 93% |

Example 11: Preparation of 5-Bromo-3-chlorosalicylic Acid

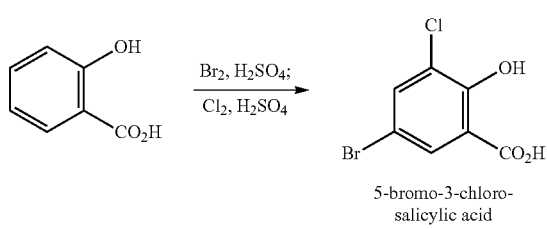 [SMILES: O=C(O)c1ccccc1O ; O=C(O)c1cc(Br)cc(Cl)c1O]

5-bromo-3-chloro-salicylic acid

Concentrated sulfuric acid (98%, 50 mL) was charged into a three-necked round bottom flask equipped with a temperature probe and a mechanical stirrer. The solution was cooled in an ice bath with stirring until an internal temperature of 5° C. was reached. Salicylic acid (15.0 g, 109 mmol) was then added portion-wise while keeping the internal temperature below 10° C. An inlet for a Teflon needle/syringe pump was then attached to the reaction flask through the remaining neck for delivering bromine. Bromine (3.2 mL, 62 mmol) was slowly added over 30 minutes during which the reaction mixture was kept below 10° C. After completion of the addition, the ice bath was removed and replaced with a heating mantle. The reaction mixture was stirred at ambient temperature for 30 minutes and was then heated to 40° C. for an additional 30 minutes. A RP-HPLC UV trace of the reaction mixture indicated the formation of 5-bromosalicylic acid with no salicylic acid remaining. The reaction mixture was diluted with concentrated sulfuric acid (98%, 151 mL). Chlorine gas was bubbled through a gas dispersion tube into the reaction mixture at 40° C. After 2.5 hours, a RP-HPLC UV trace indicated the remaining 5-bromosalicylic acid being less than 1% in the reaction mixture. The reaction mixture was cooled to 5° C., and then slowly poured over crushed ice to form solid precipitation. The resulting precipitate was filtered and the filtered solids were dissolved in ethyl acetate. The organic solution was washed with water twice, dried over anhydrous sodium sulfate, filtered, and concentrated to give yellow solids. The crude solids were further dried in a vacuum oven at 55° C. for 15 hours to afford the title compound as a yellow solid (26 g, 95%). A RP-HPLC UV trace of the solid indicated the crude material had the following composition: 5-bromo-3-chlorosalicylic acid (90%), 3,5-dibromosalicylic acid (9%) and 3-bromosalicylic acid (1%).

Example 12: Preparation of 5-Bromo-3,6-dichlorosalicylic Acid

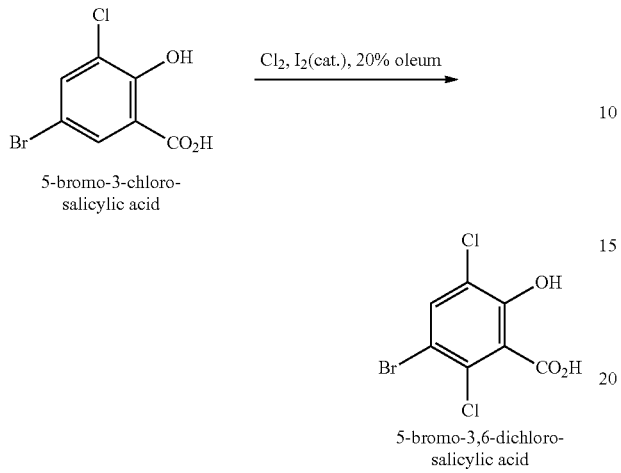

5-bromo-3-chloro-
salicylic acid 5-bromo-3,6-dichloro-
salicylic acid

Oleum (20%, 125 mL) was placed in a 250 mL three-neck round-bottom flask equipped with an overhead stirrer, a temperature probe, a gas dispersion tube and a glass exit tube inserted into a base bath of sodium hydroxide solution for trapping excess chlorine. The solution was cooled in an ice-water bath to reach an internal temperature of 5° C. 5-Bromo-3-chlorosalicylic acid (25 g, 100 mmol) and iodine (190 mg, 0.75 mmol) were added, and the reaction mixture was stirred at 5° C. with chlorine gas bubbling through the dispersion tube. After 15 minutes, the ice bath was removed and the reaction mixture was allowed to warm to ambient temperature. After 1.5 hours, the reaction mixture was heated to 33° C. with an oil bath. Another portion of iodine (190 mg, 0.75 mmol) was added to the reaction mixture after 3 hours at 33° C. During the course, chlorine was bubbled into the reaction mixture for a total of 5.5 hours. Heating and chlorine addition were stopped after 5.5 hours and the reaction mixture was cooled to 5° C. with an ice bath. The reaction mixture was poured into crushed ice (about 1200 g) with vigorous mixing and extracted with ethyl acetate (1×300 mL, 3×200 mL). The combined organic layers were washed with water (3×100 mL), brine (1×100 mL), dried over anhydrous sodium sulfate, filtered, and concentrated in vacuo to give yellow powders. The crude product was triturated in hexanes (100 mL) to afford the title compound as an off-white powder (26 g, 92%). $^1$H NMR (600 MHz, DMSO-$d_6$) indicated the material had a purity of about 81%.

Example 13: Preparation of 5-Bromo-3,6-dichlorosalicylic Acid (Alternative Conditions)

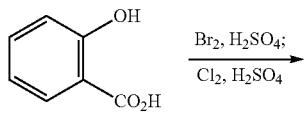

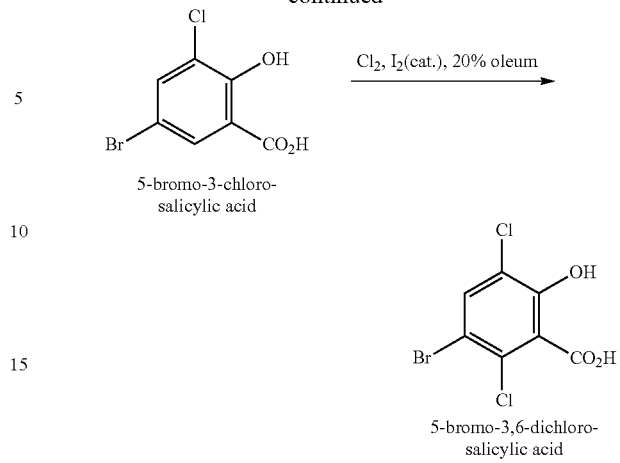

5-bromo-3-chloro-
salicylic acid 5-bromo-3,6-dichloro-
salicylic acid

Concentrated sulfuric acid (96%, 145 mL) was charged into a 1000 mL three-necked round bottom flask equipped with a temperature probe and a mechanical stirrer. The solution was cooled in an ice bath with stirring until an internal temperature of 5° C. was reached. Salicylic acid (30.0 g, 217 mmol) was then added portion-wise while keeping the internal temperature below 10° C. An inlet for a Teflon needle/syringe pump was then attached to the reaction flask through the remaining neck of the flask for delivering bromine. Bromine (6.12 mL, 119 mmol) was slowly added over 30 minutes during which the reaction mixture was kept below 10° C. After completion of the addition and removal of the ice bath, the reaction mixture was allowed to warm to ambient temperature and stirred for an additional 30 minutes. After consumption of salicylic acid as monitored by RP-HPLC, the Teflon needle/syringe pump was removed. The reaction vessel was applied with vacuum (25 to 30 mmHg) to remove excess bromine. An in-line trap of 5% aqueous sodium bisulfite was used between the reaction vessel and the vacuum for scavenging the bromine. The reaction mixture was stirred under vacuum for about 1 hour, during which time the initial orange color of the mixture became light yellow indicating that the excess bromine was removed.

The vacuum line was replaced with a gas inlet/outlet system consisting of a dispersion tube for introducing chlorine gas and a separate needle/tube outlet connected to a base trap (5% NaOH solution) for excess chlorine. Chlorine gas was bubbled into the reaction mixture at ambient temperature for an initial 30 minutes, and then the resulting mixture was heated to 45° C. Chlorine was bubbled continuously into the reaction mixture for a total of 18 hours while the temperature was maintained at 45° C. At 9 hours of chlorination, additional concentrated sulfuric acid (96%, 32 mL) was added to the reaction mixture in a single portion.

The aforementioned gas inlet/outlet system was replaced with an addition funnel, and the reaction mixture was cooled to 5° C. Fuming sulfuric acid (65% oleum, 141 mL) was added through the addition funnel over 45 minutes at a rate such that the internal temperature was kept below 20° C. At the end of addition, the reaction solvent consisted of about 20% oleum. The addition funnel was switched to the gas inlet/outlet system. Iodine crystals (827 mg, 3.36 mmol) were added and chlorine gas was bubbled into the mixture continuously. The reaction mixture was stirred at ambient temperature for 30 minutes, followed by heating at 35° C. for 6 hours.

The reaction was cooled to 5° C. and the gas inlet/outlet system was replaced with an addition funnel. Aqueous sulfuric acid solution (75%, 174 mL) was added drop-wise to the reaction mixture. After about 80 mL of aqueous sulfuric acid was added, the initial heterogeneous reaction mixture turned to almost homogeneous. At the point of about 85 mL of aqueous sulfuric acid added, gas was released and solids began precipitating from the reaction mixture accompanied by some foams. The foaming was minimized by slowing the addition rate of the sulfuric acid. Once the foaming had subsided, the remaining aqueous sulfuric acid was added at a rate such that the internal temperature was kept below 10° C. The reaction solvent consisted of about 95% sulfuric acid.

The addition funnel was removed, and the heterogeneous reaction was filtered through a fritted filter funnel (coarse porosity). The precipitate was washed with aqueous sulfuric acid (75%, 100 mL) and dried to a constant weight under vacuum. The precipitate was suspended in 5° C. cold water (100 mL) and extracted with ethyl acetate (300 mL). The organic layer was washed with water, dried over anhydrous magnesium sulfate, filtered and concentrated in vacuo to afford the title compound as an off-white solid (49 g, 79%). RP-HPLC and $^1$H NMR (600 MHz, DMSO-$d_6$) confirmed that the obtained material was 5-bromo-3,6-dichlorosalicylic acid with a purity of 88%.

Example 14: Preparation of 3,6-dichlorosalicylic Acid

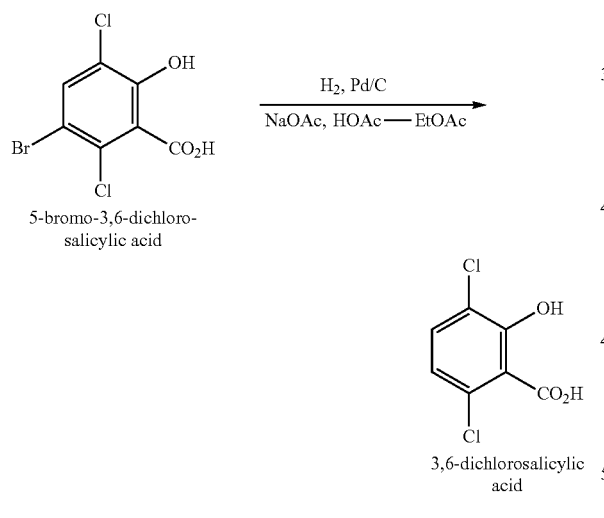

5-bromo-3,6-dichlorosalicylic acid with a purity of 88% by RP-HPLC (20.0 g, 70 mmol), sodium acetate (6.0 g, 74 mmol), and 5% Pd/C (50% water content, 8.9 g) in a 1:1 ratio solvent mixture of glacial acetic acid (140 mL) and ethyl acetate (140 mL) were charged into a 1000 mL round bottom flask. The mixture was placed under vacuum (25 to 30 mmHg), followed by purging with hydrogen. The mixture was hydrogenated (1 atmosphere) with vigorous stirring at ambient temperature for 4 hours. The resulting mixture was placed under a vacuum/purge ($N_2$) circle for 3 times, filtered through celite and washed with methanol. The filtrate was concentrated in vacuo. The remaining material was partitioned between 1.0 M HCl solution (200 mL) and ethyl acetate (200 mL), and the aqueous layer was extracted with ethyl acetate (50 mL). The combined organic layers were washed with brine (20 mL), dried over anhydrous sodium sulfate, filtered, and concentrated in vacuo to afford crude 3,6-dichlorosalicylic acid as an off-white solid (14 g, 95%) with a purity of 78% by RP-HPLC.

Crude 3,6-dichlorosalicylic acid (21.1 g, 107 mmol) was suspended in o-xylene (85 mL) in a 500 mL round bottom flask. The mixture was heated to 80° C. for 5 hours with vigorous stirring. The suspension was cooled to ambient temperature, and the solid precipitate was filtered. The precipitate was washed with hexanes and dried in vacuo to afford the title compound as a white solid (16.0 g, 77%). RP-HPLC and $^1$H NMR (600 MHz, DMSO-$d_6$) confirmed that the desired material was 3,6-dichlorosalicylic acid with a purity of 98%.

Example 15: Preparation of 3,6-dichlorosalicylic Acid

5-Bromo-3,6-dichlorosalicylic acid with a purity of 85% by RP-HPLC (10.0 g, 35.0 mmol) and 5% Pd/C (50% water content, 2.2 g) in a two-phase solvent mixture consisting of ethyl acetate (35 mL) and water (7 mL) were charged into a 100 mL round bottom flask. The mixture was placed under vacuum (25 to 30 mmHg), followed by purging with hydrogen. The mixture was hydrogenated (1 atmosphere) with vigorous stirring at ambient temperature. After 1 hour of stirring, the first portion of aqueous sodium hydroxide solution (2.5 M, 7.0 mL) was added by syringe. After 2 hours of stirring, another portion of aqueous sodium hydroxide solution (2.5 M, 5.0 mL) was added. After 3 hours of total stirring, the resulting mixture was placed under a vacuum/purge ($N_2$) circle for 3 times. The catalyst was filtered and washed with water (5 mL) and ethyl acetate (25 mL). The filtrate was transferred to a separatory funnel, and the layers were separated. The organic layer was washed with brine (5 mL), dried over anhydrous magnesium sulfate, filtered, and concentrated in vacuo to afford crude 3,6-dichlorosalicylic acid as an off-white solid (6.70 g, 93%) with a purity of 84% by RP-HPLC.

Example 16: Preparation of 5-Bromo-3,6-dichlorosalicylic Acid (Use of Iodine Monochloride Catalyst)

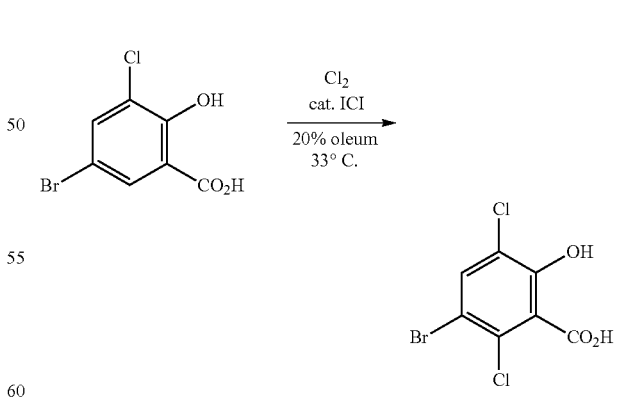

Oleum (20%, 30 mL) was placed in a 100 mL three-neck round-bottom flask equipped with an overhead stirrer, a temperature probe, a gas dispersion tube and a glass exit tube inserted into a base bath of sodium hydroxide solution for trapping excess chlorine. The solution was cooled in an ice-water bath to reach an internal temperature of 5° C.

5-Bromo-3-chlorosalicylic acid (6 g, 24 mmol) and iodine monochloride (18 µL, 0.36 mmol) were added, and the mixture was allowed to warm to ambient temperature with chlorine gas bubbling through the dispersion tube. After one hour, the reaction mixture was heated to 35° C. with an oil bath. Heating and chlorine addition were stopped after 4 hours and the reaction mixture was cooled to 5° C. with an ice bath. The mixture was poured into crushed ice with vigorous mixing and extracted with ethyl acetate (4×100 mL). The combined organic layers were washed with water (3×100 mL), brine (1×50 mL), dried over anhydrous sodium sulfate, filtered, and concentrated in vacuo to give the title compound as yellow-orange powders (6.44 g, 94%). The RP-HPLC analysis indicated that the obtained material of 5-bromo-3,6-dichlorosalicylic acid had a purity of 82%.

Example 17: Preparation of 5-Bromo-3,6-dichlorosalicylic Acid (2.25M Salicylic Acid Payload)

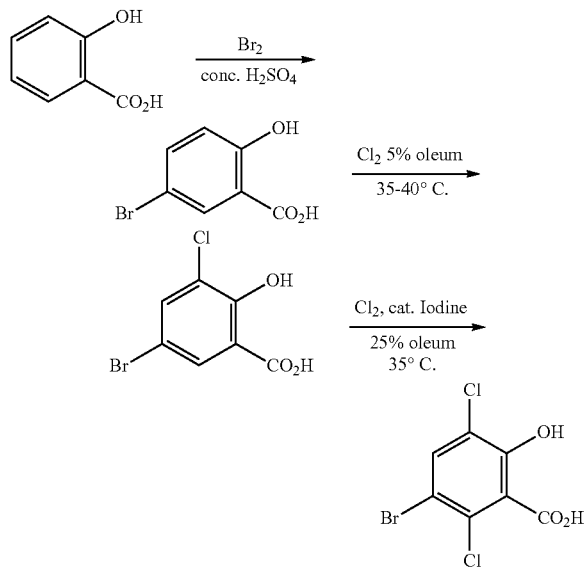

Concentrated sulfuric acid (98%, 129 mL) was charged into a 500 mL four-necked round bottom flask equipped with a temperature probe and a mechanical stirrer. The solution was cooled in an ice bath with stirring until an internal temperature of 3° C. was reached. Salicylic acid (40.0 g, 290 mmol) was then added portion-wise while keeping the internal temperature below 10° C. Bromine (8.02 mL, 157 mmol) was slowly added over 30 minutes during which time the reaction mixture was kept below 10° C. After completion of the addition of bromine and the removal of the ice bath, the reaction mixture was allowed to warm to ambient temperature and stirred for an additional 30 minutes. After consumption of the salicylic acid (monitored by RP-HPLC), the reaction vessel was placed under vacuum to remove excess bromine. The reaction mixture was stirred under vacuum for about 1.5 hours, during which time the color of the mixture changed from the initial orange to light yellow.

After the reaction mixture was cooled to 3° C., fuming sulfuric acid (65% oleum, 45 mL) was added drop-wise through the addition funnel while the internal temperature was kept below 10° C. The resulting mixture became homogenous with a final concentration of sulfuric acid of approximately 99.5%. Chlorine gas was bubbled into the reaction mixture through a gas inlet dispersion tube. A pseudo-enclosed reaction system was maintained by releasing the excess chlorine gas into a balloon attached to a gas outlet dispersion tube. The balloon was emptied about every hour by releasing the excess chlorine gas into a base trap of aqueous sodium hydroxide. The resulting mixture was heated at 35° C. for 8 hours, followed by heating to 40° C. for an additional 3 hours. After stopping the bubbling chlorine gas and heat, the mixture was cooled to 3° C.

Fuming sulfuric acid (65% oleum, 82 mL) was added drop-wise through the addition funnel while the internal temperature was kept below 20° C. At the end of the addition, the reaction solvent consisted of about 25% oleum. Iodine crystals (550 mg, 2.2 mmol) were added and chlorine gas was bubbled into the mixture through the inlet/outlet gas dispersion tubes. The reaction mixture was heated at 35° C. for 4 hours with constant stirring. The thick reaction mixture was cooled to 5° C., and aqueous sulfuric acid solution (79%, 153 mL) was added drop-wise through the addition funnel to the reaction mixture while the internal temperature was kept below 15° C. After about 40 mL of aqueous sulfuric acid was added, the release of HCl gas was observed and the initial heterogeneous reaction mixture turned to almost homogeneous burnt-orange colored solution. Vigorous bubbling and foaming was observed after the addition of 60 mL of aqueous sulfuric acid, and constant foaming occurred during the entire addition. At the end of the addition, the reaction solvent consisted of about 95.5% sulfuric acid.

The reaction mixture was filtered through a fritted filter funnel (coarse porosity). The precipitate was washed with aqueous sulfuric acid (79%, 1×200 mL, 1×100 mL) and dried under vacuum (about 30 mmHg) for one hour. The solid was suspended in 5° C. cold water (400 mL) and was stirred for 45 minutes. The filtered solids were rinsed with 1% aqueous HCl solution (1×200 mL, 1×100 mL) and dried under vacuum (about 30 mmHg) for more than 12 hours. The solid was dissolved in ethyl acetate (400 mL) and the solution was dried over anhydrous sodium sulfate, filtered and concentrated. The resulting solid was dried under high vacuum for about one hour to afford the title compound as a pale-yellow powder (66.6 g, 80.3%). The RP-HPLC analysis indicated that the obtained 5-bromo-3,6-dichlorosalicylic acid had a purity of 83%.

Example 18: Preparation of 5-Bromo-3,6-dichlorosalicylic Acid (SO₃/Salicylic Acid Molar Ratio)

Experiment 18.1: The procedure described in Example 13 was repeated using a reaction medium with a concentration of 1.5 M, 20% oleum, and 0.1 eq. of $I_2$ as the catalyst for the second chlorination step. The molar ratio of $SO_3$ to salicylic acid of the reaction medium in Experiment 18.1 was 6.3.

Experiment 18.2: The procedure described in Example 13 was repeated using a reaction medium with a concentration of 2.25 M, 20% oleum, and 1.5 mol % of $I_2$ as the catalyst for the second chlorination step. The molar ratio of $SO_3$ to salicylic acid of the reaction medium in Experiment 19.2 was 3.8. Experiment 18.2 failed to give the 5-bromo-3,6-dichlorosalicylic acid during the second chlorination of 5-bromo-3-chlorosalicylic acid.

Experiment 18.3: The procedure described in Example 17 was repeated using a reaction medium with a concentration of 2.25 M, 25% oleum, and 0.75 mol % of $I_2$ as the catalyst for the second chlorination step. The molar ratio of SO$_3$ to salicylic acid of the reaction medium in Experiment 18.2 was 5.3.

The results of Experiments 18.1, 18.2, and 18.3 are presented below in Table 18-A and suggest that a SO$_3$/salicylic acid molar ratio of at least about 4.0 or greater is generally needed in the reaction medium for suitable conversion of 5-bromo-3-chlorosalicylic acid to 5-bromo-3,6-dichlorosalicylic acid by the second chlorination.

TABLE 18-A

Effect of SO$_3$/Salicylic Acid Molar Ratio (Second Chlorination Reaction)

| EXP. NO. | SCALE (G) | CONC (M) | I$_2$ (MOL %) | MOLAR RATIO OF SO$_3$ TO SA | MASS RECOVERY (%) | SA TO BDCSA YIELD (%) | RP-HPLC PURITY (%) |
|---|---|---|---|---|---|---|---|
| 19.1 | 30 | 1.5 | 1.5 | 6.3 | 79 | 68 | 86% BDCSA; 5% TCSA; 5.3% DBCSA; 1.4% BCSA |
| 19.2 | 30 | 2.25 | 1.5 | 3.8 | — | — | |
| 19.3 | 40 | 2.25 | 0.75 | 5.3 | 85 | 71 | 84% BDCSA; 4.5% TCSA; 6.9% DBCSA; 2.9% BCSA |

Example 19: Preparation of 5-Bromo-3,6-dichlorosalicylic Acid (with Isolation of 5-Bromo-3-chlorosalicylic Acid)

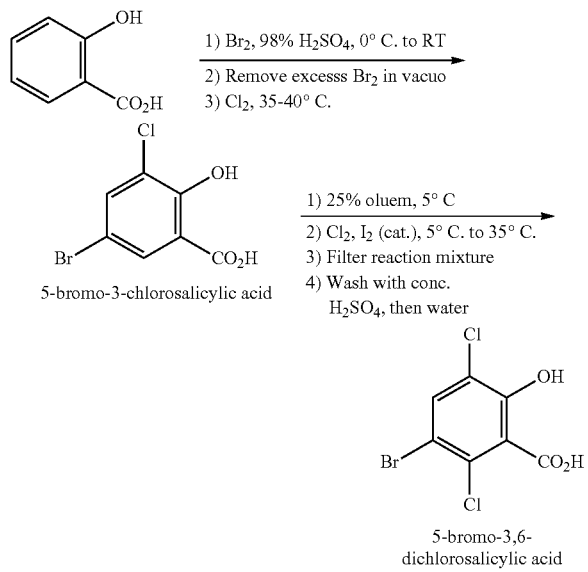

Concentrated sulfuric acid (98%, 145 mL) was charged into a 1000 mL four-necked round bottom flask equipped with a temperature probe and a mechanical stirrer. The solution was cooled in an ice bath with stirring until an internal temperature of 3° C. was reached. Salicylic acid (40.0 g, 290 mmol) was then added portion-wise while keeping the internal temperature below 10° C. Bromine (7.88 mL, 154 mmol) was slowly added over 30 minutes during which time the reaction mixture was kept below 10° C. After completion of the addition of bromine and the removal of the ice bath, the reaction mixture was allowed to warm to ambient temperature and stirred for an additional 30 minutes. After consumption of the salicylic acid (monitored by RP-HPLC), the reaction vessel was placed under vacuum to remove excess bromine. The reaction mixture was stirred under vacuum for about 1 hour, during which time the color of the mixture changed from the initial orange to off-white.

After the reaction mixture was cooled to 4° C., chlorine gas (78.1 g, 1101 mmol) was bubbled into the reaction mixture through a gas inlet dispersion tube. A pseudo-enclosed reaction system was maintained by releasing the excess chlorine gas into a balloon attached to a gas outlet dispersion tube. The balloon was emptied about every hour by releasing the excess chlorine gas into a base trap of aqueous sodium hydroxide. The resulting mixture was warmed to 40° C. over 1 hour, followed by heating at 40° C. for an additional 4.5 hours. During the reaction, the reaction mixture became substantially heterogeneous as the newly formed 5-bromo-3-chlorosalicylic acid precipitated from the reaction mixture. After stopping the bubbling chlorine gas and heat, the mixture was cooled to ambient temperature. The solids were filtered from the reaction mixture. The filtered solids were washed with concentrated sulfuric acid (98%, 30 mL) and dried under vacuum (about 30 mmHg) to provide the crude product of 5-bromo-3-chlorosalicylic acid as a form of wet cake of white solids (77.1 g).

A part of crude product (30 g) was partitioned in a mixture of water (200 mL) and ethyl acetate (100 mL), and the aqueous layer was extracted with another portion of ethyl acetate (1×100 mL). The combined organic extracts were dried over anhydrous sodium sulfate, filtered and concentrated. The resulting solid was dried under high vacuum to afford the title compound as a white solid (23.0 g) with a mass recovery yield of 76.7%. A RP-HPLC UV trace of the solid indicated the crude material had the following composition: 5-bromo-3-chlorosalicylic acid (81.1%), 5-bromosalicylic acid (12.0%), 3,5-dibromosalicylic acid (5.3%) and 3,5-dichlorosalicylic acid (1.7%).

A 20% oleum solution (129 mL) was placed in a 1000 mL four-necked round bottom flask equipped with a temperature probe and a mechanical stirrer. The solution was cooled in an ice bath with stirring until an internal temperature of 3° C. was reached. Fuming sulfuric acid (65% oleum, 22 mL) was added to bring the reaction medium to consist of about 25% oleum. The crude product of 5-bromo-3-chlorosalicylic acid, isolated described above as a form of wet cake (47 g) (i.e., containing the crude 5-bromo-3-chlorosalicylic acid of about 36 g, 144 mmol), was added portion-wise to the prepared 25% oleum solution while the internal temperature was kept below 15° C. Iodine crystals (273 mg, 1.1 mmol)

were added and chlorine gas (19.8 g, 279 mmol) was bubbled into the mixture through the inlet/outlet gas dispersion tubes. The reaction mixture was heated at 35° C. for 3.5 hours with constant stirring. The thick reaction mixture was cooled to 3° C., and filtered. The filtered solids were washed with concentrated sulfuric acid (98%, 2×100 mL), sulfuric acid solution (75%, 1×100 mL), and water (1×100 mL). Additional solids formed in the filtrates from the concentrated sulfuric acid wash and filtered. The resulting filtered solids were washed with sulfuric acid solution (75%, 1×50 mL) and water (1×50 mL). The combined solids were dried under high vacuum overnight to afford the title compound as a white powder (32.5 g, 70%). The RP-HPLC analysis indicated that the obtained 5-bromo-3,6-dichlorosalicylic acid had a purity of 89%.

The 5-bromo-3,6-dichlorosalicylic acid material, prepared by the direct filtration described above, was subjected to the debromination reaction. The reaction was carried out with the procedure described in Example 15 in a 4:1 mixture of ethyl acetate and water. The desired product of 3,6-dichlorosalicylic acid was obtained without a need for an additional process of crude 5-bromo-3,6-dichlorosalicylic acid.

Example 20: Preparation of 5-Bromo-3,6-dichlorosalicylic Acid (With or Without Isolation of 5-Bromo-3-chlorosalicylic Acid)

Experiment 20.1: The procedure described in Example 17 was repeated, wherein the acidic reaction medium for the second chlorination was modified to provide an acidic reaction medium comprising 25% oleum after formation of 5-bromo-3-chlorosalicylic acid without isolating the 5-bromo-3-chlorosalicylic acid product from the first chlorination.

Experiment 20.2: The same experiment in Example 19 was presented, wherein the 5-bromo-3-chlorosalicylic acid product from the first chlorination was isolated and placed in the acidic reaction medium comprising 25% oleum for the second chlorination.

The results of Experiments 20.1 and 20.2 are presented below in Table 20-A and suggest that the isolation of 5-bromo-3-chlorosalicylic acid may improve the purity of 5-bromo-3,6-dichlorosalicylic acid from the second chlorination.

Example 21: Preparation of 5-Bromo-3,6-dichlorosalicylic Acid (Chlorine Gas Equivalents)

The equivalents of the chlorine gas were controlled by recovering the unreacted chlorine gas overhead and recycling back into the reaction medium. The amount of chlorine gas used during the reaction was measured by weighing the chlorine gas tank before and after the reaction.

Experiment 21.1: The procedure described in Example 8 was repeated except that the reaction temperature was kept at 33° C. and 1.5 mole % of iodine catalyst was used for converting 5-bromo-salicylic acid to 5-bromo-3,6-dichlorosalicylic acid.

Experiment 21.2: The procedure described in Example 12 was repeated for converting 5-bromo-3-chlorosalicylic acid to 5-bromo-3,6-dichlorosalicylic acid.

Experiment 21.3: The procedure described in Example 17 was repeated for converting 5-bromo-salicylic acid to 5-bromo-3,6-dichlorosalicylic acid.

Experiment 21.4: The procedure described in Example 17 was repeated for converting 5-bromo-salicylic acid to 5-bromo-3,6-dichlorosalicylic acid.

Experiment 21.5: The same experiment in Example 19 was presented for converting 5-bromo-salicylic acid to 5-bromo-3,6-dichlorosalicylic acid.

The results of Experiments 21.1, 21.2, 21.3, 21.4, and 21.5 are presented below in Table 21-A and suggest that the total chlorine equivalents were controlled from about 2.0 to about 6.0 equivalents related to 5-bromo-salicylic acid for converting 5-bromo-salicylic acid to 5-bromo-3,6-dichlorosalicylic acid.

TABLE 21-A

| | Chlorine Gas Equivalents | | | | | |
|---|---|---|---|---|---|---|
| EXP. NO. | SCALE (G) | CONC (M) | $I_2$ (MOL %) | $Cl_2$ (Eq.) SA to BCSA | $Cl_2$ (Eq.) BCSA to BCSA | Total $Cl_2$ (Eq.) SA TO BDCSA |
| | Stoichiometry ($Cl_2$ to substrate) | | | 1.0 | 1.0 | 2.0 |
| 21.1 | 25 | 0.46 | 1.5 | — | — | 2.84 |
| 21.2 | 25 | 0.80 | 1.5 | — | 2.21 | — |
| 21.3 | 40 | 2.25 | 0.6 | 1.20 | 1.82 | 3.02 |

TABLE 20-A

Purity Comparison of 5-bromo-3,6-dichlorosalicylic acid with or without isolation of 5-bromo-3-chlorosalicylic acid

| EXP. NO. | SCALE (G) | CONC (M) | $I_2$ (MOL %) | MASS RECOVERY (%) | SA TO BDCSA YIELD (%) | BCSA to BDCSA YIELD (%) | RP-HPLC PURITY (%) |
|---|---|---|---|---|---|---|---|
| 20.1 | 40 | 2.25 | 0.75 | 90 | 67 | — | 75% BDCSA; 9.4% TCSA; 6.7% DBCSA; 2.2% BCSA |
| 20.2 | 40 | 2.00 | 0.75 | 79 | — | 70 | 89% BDCSA; 1.7% TCSA; 6.6% DBCSA; 2.1% BCSA |

TABLE 21-A-continued

| | | | | Chlorine Gas Equivalents | | |
|---|---|---|---|---|---|---|
| EXP. NO. | SCALE (G) | CONC (M) | $I_2$ (MOL %) | $Cl_2$ (Eq.) SA to BCSA | $Cl_2$ (Eq.) BCSA to BCSA | Total $Cl_2$ (Eq.) SA TO BDCSA |
| 21.4 | 40 | 2.25 | 0.5 | — | — | 2.63 |
| 21.5 | 40 | 2.00 | 0.75 | 3.80 | 1.95 | 5.75 |

Example 22: Preparation of Methyl 3-Bromo-2,5-dichloro-6-methoxybenzoate

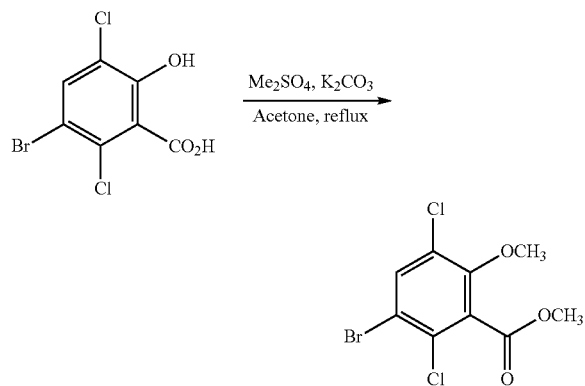

5-Bromo-3,6-dichlorosalicylic acid with a purity of 81% by RP-HPLC (32 g, 112 mmol) was dissolved in acetone (340 mL), followed by additions of anhydrous potassium carbonate (38.6 g, 280 mmol) and dimethyl sulfate (24.6 mL, 258 mmol). The resulting reaction mixture was heated to reflux for 2 hours. The mixture was cooled to ambient temperature and filtered. The filtered solids were washed with acetone, and the combined organic filtrates were concentrated. The resulting brownish oil was partitioned in ethyl acetate and saturated sodium bicarbonate. The organic layer was dried over anhydrous magnesium sulfate and concentrated to afford the title compound as a brown oil (38 g). The RP-HPLC analysis indicated that the obtained crude methyl 3-Bromo-2,5-dichloro-6-methoxybenzoate had a purity of 85% and contained the excess dimethyl sulfate.

It can be purified by vacuum distillation. The crude methyl 3-Bromo-2,5-dichloro-6-methoxybenzoate (38 g) was placed in a flask and heated to 50° C. A short vigreux column and a distillation head were attached to the system and a vacuum (~2-3 mmHg) was applied. The mixture was heated to 100° C. to first remove the excess dimethyl sulfate, and then heated to 180° C. The fractions were collected while the remaining oil in the flask was heated from 180° C. to 270° C. The RP-HPLC analysis and $^1$H NMR indicated that the distilled, nearly colorless oil, was the desired product of methyl 3-Bromo-2,5-dichloro-6-methoxybenzoate (31 g, 88%) with a purity of 81%. $^1$H-NMR (600 MHz, CDCl$_3$) δ 7.3 (s, 1H), 4.0 (s, 3H), 3.9 (s, 3H).

Example 23: Preparation of Methyl 2,5-Dichloro-6-methoxybenzoate

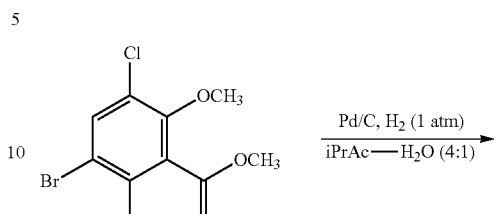

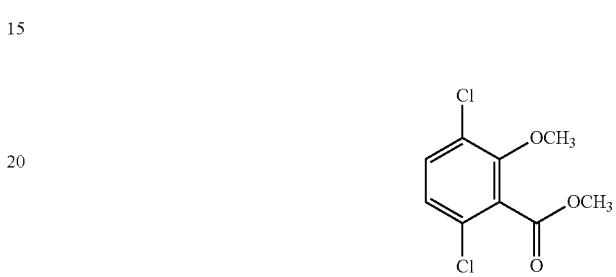

3-Bromo-2,5-dichloro-6-methoxybenzoate with a purity of 81% by RP-HPLC (5.0 g, 15.9 mmol) and 5% Pd/C (50% water content, 1.0 g) in a two-phase solvent mixture consisting of isopropyl acetate (17 mL) and water (4 mL) were charged into a 100 mL round bottom flask. The mixture was placed under vacuum (25 to 30 mmHg), followed by purging with hydrogen. The mixture was hydrogenated (1 atmosphere) with vigorous stirring at ambient temperature for 1.5 hour. After consumption of the 3-Bromo-2,5-dichloro-6-methoxybenzoate (monitored by RP-HPLC), the catalyst was filtered and washed with water (5 mL) and ethyl acetate (25 mL). The filtrate was transferred to a separatory funnel, and the layers were separated. The aqueous layer was extracted with ethyl acetate, and the combined organic layers were dried over anhydrous magnesium sulfate, filtered, and concentrated in vacuo to afford crude methyl 2,5-dichloro-6-methoxybenzoate as a yellow solid (3.5 g, 91%) with a purity of 71%. ESI-MS m/z 235 (M+H).

Examples 24 through 27 describe the preparation of 3,6-dichloro-2-hydroxybenzoic acid (which can be further converted to dicamba) from 5-bromo-3-chloro-2-hydroxybenzaldehyde as illustrated in the scheme shown below:

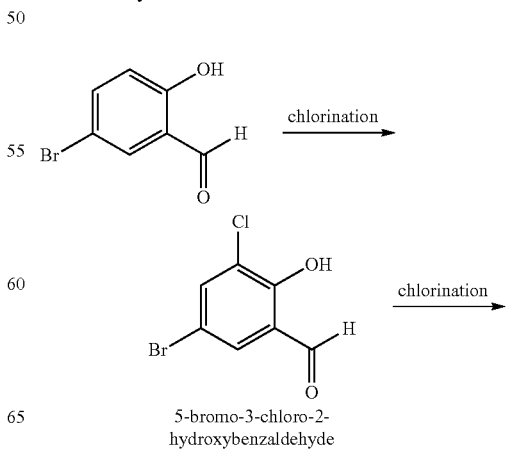

5-bromo-3-chloro-2-hydroxybenzaldehyde

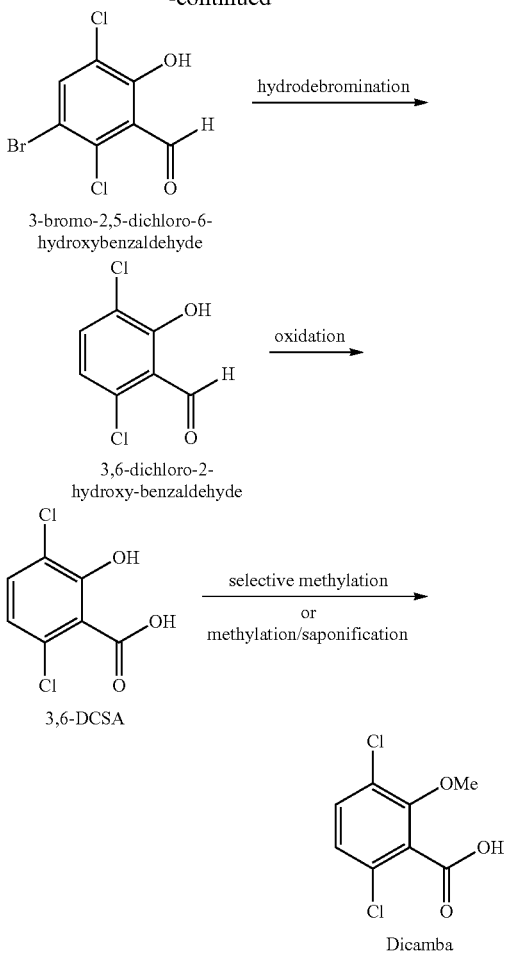

3-bromo-2,5-dichloro-6-hydroxybenzaldehyde 3,6-dichloro-2-hydroxy-benzaldehyde 3,6-DCSA

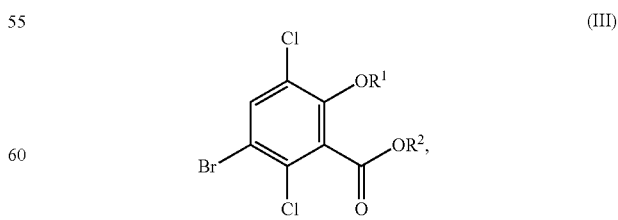

Dicamba

Example 24: Preparation of 5-Bromo-3-chloro-2-hydroxybenzaldehyde

5-Bromo-2-hydroxybenzaldehyde (5.0 g, 24.9 mmol) was dissolved in acetic acid (100 mL). Chlorine gas was continuously bubbled into the solution while stirring for 4 hours at ambient temperature. The acetic acid was largely removed in vacuo and the solids were partitioned in water (100 mL) and ethyl acetate (100 mL). The organic layer was washed with water (1×50 mL), dried over anhydrous sodium sulfate, filtered, and concentrated in vacuo to yield the title compound (5.4 g, 93%). Analytical data for 5-bromo-3-chloro-2-hydroxybenzaldehyde: $^1$H (300 MHz, CDCl$_3$) 11.20, 9.84, 7.7, 7.6.

Example 25: Preparation of 3-Bromo-2,5-dichloro-6-hydroxybenzaldehyde

5-Bromo-3-chloro-2-hydroxybenzaldehyde (2.0 g, 8.5 mmol) was dissolved in oleum (20%, 50 mL). Iodine (0.03 g, 0.12 mmol) was added and the resulting solution was stirred at 35° C. for 24 hours while chlorine gas was bubbling into the solution. The reaction mixture was poured onto crushed ice (about 100 g), and the resulting suspension was extracted with ethyl acetate (3×100 mL). After drying over anhydrous sodium sulfate, solvent was removed in vacuo to give the title product (1.7 g, 73%). Analytical data for 3-bromo-2,5-dichloro-6-hydroxybenzaldehyde: $^1$H NMR (300 MHz, DMSO-d$_6$) 12.2, 10.3, 8.2.

Example 26: Preparation of 3,6-Dichloro-2-hydroxybenzaldehyde

3-Bromo-2,5-dichloro-6-hydroxybenzaldehyde (1.0 g, 3.7 mmol), potassium acetate (0.38 g, 3.9 mmol) and Pd/C (5%, 0.1 g) were added to acetic acid (25 mL). After the system was purged under a vacuum, the mixture was stirred under hydrogen (1 atm) for 18 hours. The reaction mixture was filtered over celite and the acetic acid was largely removed in vacuo. The solids were partitioned in ethyl acetate (25 mL) and water (25 mL). The organic layer was dried over anhydrous sodium sulfate, filtered, and concentrated to yield the title product as a yellow solid (0.46 g, 65%). Analytical data for 3,6-dichloro-2-hydroxybenzaldehyde: $^1$H NMR (300 MHz, DMSO-d$_6$) 12.1, 10.3, 7.8, 7.1.

Example 27: Preparation of 3,6-Dichloro-2-hydroxybenzoic Acid 3,6-Dichloro-2-hydroxybenzaldehyde (0.050 g, 0.26 mmol), sulfamic acid (0.035 g, 0.37 mmol) and sodium dihydrogenphosphate (0.12 g, 1.0 mmol) were dissolved in a mixture of dioxane (2 mL) and water (1 mL). The mixture was cooled to 0° C. and sodium chlorite trihydrate (0.04 g, 0.3 mmol) in water (0.2 mL) was added. The cooling bath was removed, and the mixture was stirred for one hour at ambient temperature. The solvents were largely removed in vacuo and the concentrate was diluted with water (10 mL). The pH of the solution was adjusted to pH=about 1 with concentrated hydrochloric acid and was extracted with ethyl acetate (2×10 mL). The extract was dried over anhydrous sodium sulfate, filtered, and concentrated to give the title product as an off-white solid (0.047 g, 88%). The RP-HPLC and $^1$H NMR analyses confirmed that the obtained material was 3,6-dichloro-2-hydroxybenzoic acid.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed is:

1. A process for the preparation of a compound corresponding in structure to Formula (III):

(III)

or a salt thereof, the process comprising:
contacting a compound corresponding in structure to Formula (II):

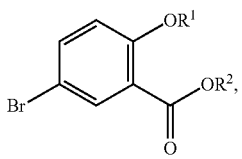

(II)

or a salt thereof, with a chlorinating agent in an acidic reaction medium to provide the compound or salt of Formula (III);

wherein $R^1$ is hydrogen or $C_{1-6}$-alkyl;

$R^2$ is hydrogen or $C_{1-6}$-alkyl; and the compound or salt of Formula (II) is contacted with about 2.0 to about 8.0 active chlorine equivalents of the chlorinating agent.

2. The process of claim 1, wherein the chlorinating agent is chlorine gas.

3. The process of claim 1, wherein the reaction medium comprises sulfuric acid.

4. The process of claim 1, wherein the reaction medium comprises oleum.

5. The process of claim 1, wherein the reaction medium is maintained at a temperature from about 0° C. to about 100° C. during the contacting step.

6. The process of claim 1, wherein the process further comprises selectively debrominating the compound or salt of Formula (III) to provide a compound corresponding in structure to Formula (IV):

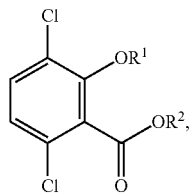

(IV)

or a salt thereof; wherein $R^1$ is hydrogen or $C_{1-6}$-alkyl; and $R^2$ is hydrogen or $C_{1-6}$-alkyl.

7. The process of claim 1, wherein the process further comprises the step of brominating a compound corresponding in structure to Formula (I):

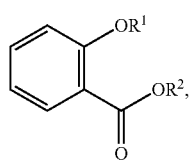

(I)

or a salt thereof, to provide the compound or salt of Formula (II); wherein $R^1$ is hydrogen or $C_{1-6}$-alkyl; and $R^2$ is hydrogen or $C_{1-6}$-alkyl.

8. A process for the preparation of a compound corresponding in structure to Formula (III):

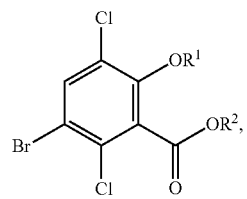

(III)

or a salt thereof, the process comprising:

contacting a compound corresponding in structure to Formula (I):

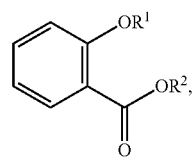

(I)

or a salt thereof, with a brominating agent in an acidic reaction medium comprising sulfuric acid to provide the compound corresponding in structure to Formula (II):

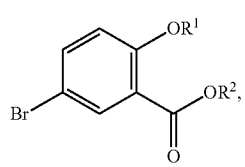

(II)

or a salt thereof;

contacting the compound or salt of Formula (II) with a first chlorinating agent without first isolating the compound or salt of Formula (II) from the acidic reaction medium to provide a compound corresponding in structure to Formula (VI):

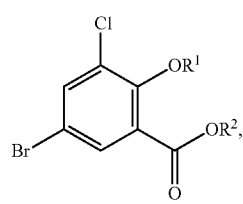

(VI)

or a salt thereof; and contacting the compound or salt of Formula (VI) with a second chlorinating agent to provide the compound or salt of Formula (III);

wherein:

$R^1$ is hydrogen or $C_{1-6}$-alkyl;

$R^2$ is hydrogen or $C_{1-6}$-alkyl; and the first chlorinating agent and the second chlorinating agent can be the same or different.

9. The process of claim 8, wherein the process further comprises modifying the acidic reaction medium after formation of the compound or salt of Formula (VI) by providing oleum to the acidic reaction medium after formation of the compound or salt of Formula (VI), and contacting the compound or salt of Formula (VI) with the second chlorinating agent without first isolating the compound or salt of Formula (VI) from the reaction medium to provide the compound of Formula (III);

wherein:
R¹ is hydrogen or $C_{1-6}$-alkyl;
R² is hydrogen or $C_{1-6}$-alkyl; and
the first chlorinating agent and the second chlorinating agent can be the same or different.

10. The process of claim 8, wherein the compound or salt of Formula (VI) is isolated from the reaction mixture and subsequently contacted with the second chlorinating agent to provide the compound or salt of Formula (III).

11. The process of claim 6, wherein R¹ is other than methyl and/or R² is other than hydrogen; and the process further comprises
converting the compound or salt of Formula (IV) to a compound corresponding in structure to Formula (V):

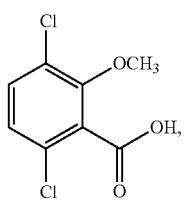

(V)

or a salt thereof.

12. The process of claim 6, wherein R¹ and R² are both hydrogen; and the process further comprises:
(i) methylating a compound corresponding in structure to Formula (IV-1):

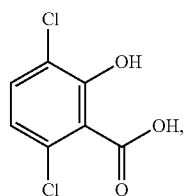

(IV-1)

or a salt thereof; to provide a compound corresponding in structure to Formula (IV-2):

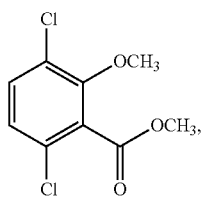

(IV-2)

or a salt thereof; and
saponifying the compound or salt of Formula (IV-2) to provide a compound corresponding in structure to Formula (V):

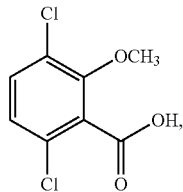

(V)

or a salt thereof;
or (ii) selectively methylating the compound or salt of Formula (IV-1) to provide the compound or salt of Formula (V).

13. The process of claim 8; wherein R¹ and R² are both hydrogen; and the process further comprises:
selectively debrominating a compound corresponding in structure to Formula (III-1):

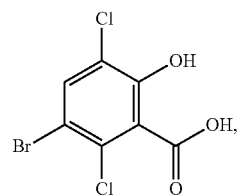

(III-1)

or a salt thereof; to provide a compound corresponding in structure to Formula (IV-1):

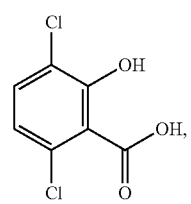

(IV-1)

or a salt thereof; and
(i) methylating the compound or salt of Formula (IV-1) to provide a compound corresponding in structure to Formula (IV-2):

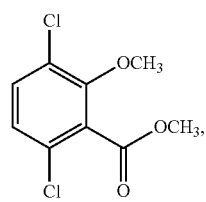

(IV-2)

or a salt thereof; and
saponifying the compound or salt of Formula (IV-2) to provide a compound corresponding in structure to Formula (V):

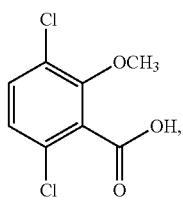

(V)

or a salt thereof;

or (ii) selectively methylating the compound or salt of Formula (IV-1) to provide the compound or salt of Formula (V).

14. The process of claim 1, wherein $R^1$ and $R^2$ are both hydrogen; and the process further comprises:

contacting a compound corresponding in structure to Formula (III-1):

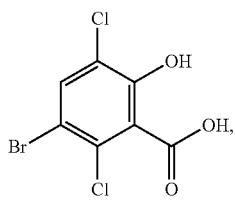

(III-1)

or a salt thereof, with a methylating agent to provide a compound corresponding in structure to Formula (III-2):

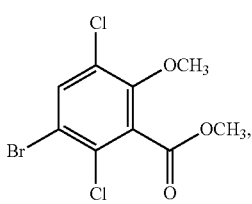

(III-2)

or a salt thereof;

selectively debrominating the compound or salt of Formula (III-2) to provide a compound corresponding in structure to Formula (IV-2):

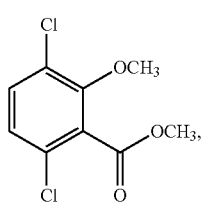

(IV-2)

or a salt thereof; and saponifying the compound or salt of Formula (IV-2) to provide a compound corresponding in structure to Formula (V):

(V)

or a salt thereof.

15. The process of claim 8, wherein $R^1$ and $R^2$ are both hydrogen; and the process further comprises:

contacting a compound corresponding in structure to Formula (III-1):

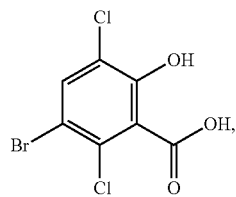

(III-1)

or a salt thereof, with a methylating agent to provide a compound corresponding in structure to Formula (III-2):

(III-2)

or a salt thereof;

selectively debrominating the compound or salt of Formula (III-2) to provide a compound corresponding in structure to Formula (IV-2):

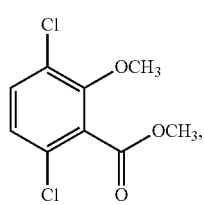

(IV-2)

or a salt thereof; and saponifying the compound or salt of Formula (IV-2) to provide a compound corresponding in structure to Formula (V):

(V)

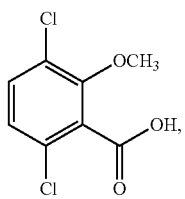

or a salt thereof.

16. A process for the preparation of a compound corresponding in structure to Formula (V):

(V)

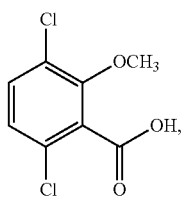

or a salt thereof, the process comprising:
contacting a compound corresponding in structure to Formula (VII):

(VII)

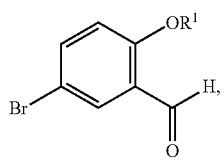

or a salt thereof, with a chlorinating agent to provide a compound corresponding in structure to Formula (VIII):

(VIII)

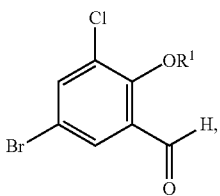

or a salt thereof; contacting the compound or salt of Formula (VIII) with a chlorinating agent to provide a compound corresponding in structure to Formula (IX):

(IX)

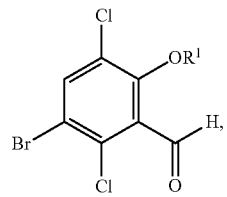

or a salt thereof; contacting the compound or salt of Formula (IX) with a debrominating agent to provide a compound corresponding in structure to Formula (X):

(X)

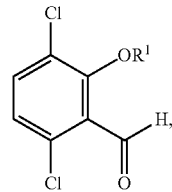

or a salt thereof, contacting the compound or salt of Formula (X) with an oxidizing agent to provide a compound corresponding in structure to Formula (IV-1):

(IV-1)

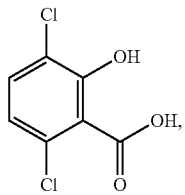

or a salt thereof; and converting the compound or salt of Formula (IV-1) to the compound or salt of Formula (V);
wherein $R^1$ is hydrogen or $C_{1-6}$-alkyl.

17. The process of claim 16, wherein $R^1$ is hydrogen, and the process further comprises:
methylating the compound or salt of Formula (IV-1) to provide a compound corresponding in structure to Formula (IV-2):

(IV-2)

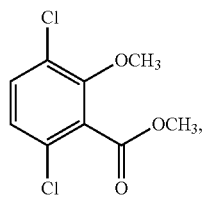

or a salt thereof; and
saponifying the compound or salt of Formula (IV-2) to provide the compound or salt of Formula (V).

18. The process of claim 16, wherein $R^1$ is hydrogen, and the process further comprises selectively methylating the compound or salt of Formula (IV-1) to provide the compound or salt of Formula (V).

* * * * *